(12) United States Patent
Navarro Y Garcia et al.

(10) Patent No.: US 10,016,510 B2
(45) Date of Patent: *Jul. 10, 2018

(54) IMMUNOGENIC COMPOSITION IN EMULSION FORM

(71) Applicant: Commissariat à l'énergie atomique et aux énergies alternatives, Paris (FR)

(72) Inventors: Fabrice Navarro Y Garcia, Fontaine (FR); Thomas Courant, Meylan (FR); Isabelle Texier-Nogues, Grenoble (FR); Patrice Marche, Meylan (FR)

(73) Assignee: COMMISSARIAT À L'ÉNERGIE ATOMIQUE ET AUX ÉNERGIES ALTERNATIVES, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/770,109

(22) PCT Filed: Feb. 26, 2014

(86) PCT No.: PCT/EP2014/053772
§ 371 (c)(1),
(2) Date: Aug. 25, 2015

(87) PCT Pub. No.: WO2014/131809
PCT Pub. Date: Sep. 4, 2014

(65) Prior Publication Data
US 2016/0030586 A1    Feb. 4, 2016

(30) Foreign Application Priority Data

Feb. 26, 2013  (FR) .................... 13 51687

(51) Int. Cl.
*A61K 47/48* (2006.01)
*A61K 39/39* (2006.01)
*C07K 16/28* (2006.01)
*A61K 39/00* (2006.01)
*C07K 16/02* (2006.01)
*A61K 9/107* (2006.01)
*A61K 9/00* (2006.01)

(52) U.S. Cl.
CPC .... *A61K 47/48061* (2013.01); *A61K 39/0005* (2013.01); *A61K 39/39* (2013.01); *A61K 47/48215* (2013.01); *A61K 47/48792* (2013.01); *C07K 16/02* (2013.01); *C07K 16/2863* (2013.01); *A61K 9/0019* (2013.01); *A61K 9/1075* (2013.01); *A61K 2039/55555* (2013.01); *A61K 2039/55566* (2013.01); *A61K 2039/55572* (2013.01); *A61K 2039/55583* (2013.01); *A61K 2039/57* (2013.01); *A61K 2039/572* (2013.01); *A61K 2039/6093* (2013.01); *A61K 2039/627* (2013.01); *A61K 2039/645* (2013.01); *C07K 2317/10* (2013.01); *C07K 2317/21* (2013.01)

(58) Field of Classification Search
None
See application file for complete search history.

(56) References Cited

U.S. PATENT DOCUMENTS

| | | | |
|---|---|---|---|
| 6,080,725 | A | 6/2000 | Marciani |
| 9,150,649 | B2 * | 10/2015 | Singh ............... A61K 47/48384 |
| 2002/0051748 | A1 | 5/2002 | Snow et al. |
| 2009/0220547 | A1 | 9/2009 | Contorni |
| 2011/0201695 | A1 | 8/2011 | Mourier-Robert et al. |
| 2014/0112950 | A1 | 4/2014 | Singh et al. |
| 2015/0057374 | A1 * | 2/2015 | Couffin .................. A61K 47/24 514/785 |
| 2015/0258022 | A1 | 9/2015 | Navarro Y Garcia et al. |
| 2016/0030586 | A1 | 2/2016 | Navarro Y Garcia et al. |

FOREIGN PATENT DOCUMENTS

| | | |
|---|---|---|
| EP | 3 103 485 | 12/2016 |
| WO | WO-93/00160 | 1/1993 |

OTHER PUBLICATIONS

International Search Report for PCT/EP2014/053772 dated May 28, 2014.
Almeida Antonio J et al: "Peptide-loaded solid lipid nanoparticles (SLN): Influence of production parameters", International Journal of Pharmaceutics (Amsterdam), vol. 149, No. 2, 1997, pp. 255-265.
Teixeira, et al., "Submicron Cationic Emulsions as a New Delivery System for Oligonucleotides", 1999, pp. 30-36, vol. 16, No. 1, Pharmaceutical Research.
Verzijlbergen, "A Barcode Screen for Epigenetic Regulators Reveals Role for the NuB4/HAT-B Histone Acetyltransferase Complex in Histone Turnover", Oct. 2011, pp. 1-15, vol. 7, No. 10, PLoS Genetics.
Notification of Transmission of International Search Report and Opinion, PCT application PCT/EP2016/078126, dated Feb. 14, 2017.

* cited by examiner

*Primary Examiner* — Tigabu Kassa
(74) *Attorney, Agent, or Firm* — B. Aaron Schulman, Esq.; Stites & Harbison, PLLC.

(57) ABSTRACT

The present invention relates to an immunogenic composition comprising a continuous aqueous phase and a dispersed phase as droplets and comprising:
  an amphiphilic lipid,
  a solubilizing lipid comprising at least one fatty acid glyceride,
  a co-surfactant comprising at least one chain consisting of alkylene oxide units,
  a surfactant bearing an antigen of the following formula (I):

$$(L_1\text{-}X_1\text{—}H_1\text{—}Y_1)_v\text{-}G\text{-}Z_1\text{—}Ag \quad (I),$$

to its preparation method and its uses, notably for producing antibodies, as a drug or in an immunization method.

7 Claims, 8 Drawing Sheets

IMMUNOGENIC COMPOSITION IN EMULSION FORM

The present invention relates to an immunogenic composition as an emulsion comprising a continuous aqueous phase and a dispersed lipid phase as droplets and comprising an antigen covalently bound to said droplets, to its preparation method and its uses, notably for producing antibodies, as a drug or in an immunization method.

The use of solid lipid emulsions or nanoparticles for delivering therapeutic agents is known from the literature.

In particular, patent application WO 2010/018223 describes the use of a formulation as a nanoemulsion, comprising a continuous aqueous phase and at least one dispersed phase comprising an amphiphilic lipid, a solubilizing lipid, a therapeutic agent and a co-surfactant comprising at least one chain consisting of alkylene oxide units, for delivering an amphiphilic or lipophilic therapeutic agent. The therapeutic agent may optionally be grafted to the co-surfactant. The therapeutic agent may notably be an immunologic agent or a vaccine. An embodiment specifically describing the use of an immunologic agent grafted to the co-surfactant or of a vaccine grafted to the co-surfactant is however not described. Further, the present inventors have shown that all the formulations described in WO 2010/018223 cannot be easily adapted when the intention is to covalently graft an antigen to the droplets of the emulsions, such grafting can only be carried out under specific conditions, in particular with a specific molar ratio (co-surfactant grafted by the antigen)/(co-surfactant grafted by the antigen+non-grafted free co-surfactant).

Almeida et al. (Int. J. Pharm. 149 (1997) 255-265) suggest that solid lipid nanoparticles may be a good alternative as a vector of antigens for delivering vaccines. In order to study the feasibility of incorporating antigens of the protein type, they incorporated a model protein (lysozyme) in solid lipid nanoparticles of 600 nm notably comprising solubilizing lipids of the Witepsol E 85 and/or Softisan 142 type, amphiphilic lipids of the Tween 80 type and co-surfactants of the Superpolystate or Poloxamer 182 or 188 type.

Müller et al. (Eur. J. Pharm. Biopharm. 50 (2000) 161-177) is a review on the use of solid lipid nanoparticles for controlled delivery of therapeutic agents and as an adjuvant for vaccines.

Saraf et al. (Vaccine 24 (2006) 45-56) describes a double water-in-oil-in-water emulsion with a diameter of more than 1 μm and comprising:
  a surface antigen of hepatitis B, soluble in water, and located in the internal aqueous phase of the double emulsion,
  soya lecithin located in the oily phase,
  optionally stearylamine as a cationic lipid.

De Temmerman et al. (Drug Discovery Today 16 (2011) 13/14, 569-582) and Krishmamachari et al. (Parm. Res. 28 (2011) 215-236) are reviews reporting that nanoemulsions may encapsulate antigens and be used as vectors for vaccines. In the second publication, reference is made to the work of:
  Shi et al. who prepared a nanoemulsion with a diameter of 20-30 nm and comprising CpG and the MG7 antigen, Span 80 and Tween 80 as amphiphilic lipids and soya oil.
  Wei et al. who prepares a nanoemulsion with a diameter of 20 nm and comprising antigens associated with the tumours (TAA), MAGE-1 and/or MAGE-3, a thermal shock protein HSP70, a staphylococcic enterotoxin A (SEA), Pluronic® 88 as a co-surfactant, Span 20 as an amphiphilic lipid and soya oil.

In these articles, the antigen (or the model protein in Almeida et al.) is encapsulated in the droplets of the emulsion and is not covalently bound to the droplets of the emulsion.

Now, an oil-in-water emulsion, for which the dispersed phase droplets comprise an encapsulated antigen may:
  be difficult to prepare. In particular, only amphiphilic or lipophilic antigens may easily be encapsulated in droplets, hydrophilic antigens requiring the production of a double emulsion with a risk of a leak towards the continuous aqueous phase. It may also be necessary to adapt the lipid components of the emulsion for each antigen which is intended to be encapsulated, which is expensive and is an obstacle to industrial use,
  may be used with difficulty for producing antibodies, as a drug or in an immunization method, notably because of "burst release" problems which are difficult to control for hydrophilic antigens (by "burst release" is meant that a non-negligible fraction of the antigen is released from the droplets by simple diffusion in a biological medium) (Demento, Biomaterials, 33 (2012) 4957-4964).

Therefore, there exists a need for providing alternative immunogenic compositions to the existing ones, and having at least one of the following advantages:
  being able to be easily used for producing antibodies, as a drug or in an immunization method,
  be stable during storage, notably by avoiding the leak of the antigen out of the droplets,
  being able to be easily prepared, notably by using industrial methods and without it being necessary to adapt the preparation method and the components of the emulsion for each antigen.
  having a small size (hydrodynamic diameter <200 nm) for facilitating cell capture by immune cells and their lymphatic drainage (Bachmann et al., Nature Reviews Immunology, 2010, 10, 787).

[Immunogenic Composition]

According to a first object, the invention relates to an immunogenic composition comprising a continuous aqueous phase and a dispersed phase as droplets and comprising:
  an amphiphilic lipid,
  a solubilizing lipid comprising at least one fatty acid glyceride,
  a co-surfactant comprising at least one chain consisting of alkylene oxide units,
  a surfactant bearing an antigen of the following formula (I):

$$(L_1\text{-}X_1\text{—}H_1\text{—}Y_1)_v\text{-}G\text{-}Z_1\text{—}Ag \qquad (I),$$

wherein:
  $L_1$ represents a lipophilic group,
  $X_1$, $Y_1$, $Z_1$ and G represent independently a binding group,
  $H_1$ represents a hydrophilic group comprising a polyalkoxylated chain,
  v is an integer from 1 to 8, and
  Ag represents an antigen,
  wherein the molar ratio of the surfactant bearing an antigen of formula (I) over the sum of the co-surfactant and of the surfactant bearing an antigen of formula (I) is from 0.01% to 5%.

The inventors have shown that vectorisation of an antigen by droplets according to the invention gave the possibility of increasing and of improving the immune response directed against said antigen. The immune response obtained after injecting an antigen vectorised by the droplets according to the invention is notably significantly more significant and more homogenous than the immune response obtained after injecting the antigen alone. The immunogenic composition may therefore be considered as an adjuvant formulation of an antigen. The use of the droplets according to the invention is therefore particularly adapted for efficiently producing antibodies directed against an antigen, as well as in the treatment of infectious pathologies, of allergy or cancers, depending on the nature of the antigen included in the immunogenic composition.

The immunogenic composition appears as an oil-in-water emulsion, preferably an oil-in-water nanoemulsion. The emulsion may be simple or multiple, notably by including in the dispersed phase a second aqueous phase.

Definitions

In the sense of the present application, the expression "dispersed phase" means the droplets comprising the optional oil/solubilizing lipid/amphiphilic lipid/co-surfactant/optional lipophilic agent of interest/surfactant bearing an antigen of formula (0/optional immunostimulating agent/ optional biological targeting ligand (free or grafted to the co-surfactant)/optional cationic surfactant. The dispersed phase is generally free of any aqueous phase. The immunogenic composition is typically free of liposomes.

The term of "droplet" encompasses both liquid oil droplets, strictly speaking, as well as solid particles from emulsions of the oil-in-water type in which the dispersed phase is solid. The abbreviation LNP is also used for designating the droplets when their size is nanometric (for "lipid nanoparticle").

The droplets of the immunogenic composition are advantageously monodispersed. The standard deviation between the minimum and maximum diameters of the droplets relatively to the average diameter is generally less than or equal to 30%, preferably 20%. The average diameter of the droplets of the dispersed phase is preferably from 20 to 200 nm, notably from 40 to 150 nm and in particular from 50 to 150 nm. These diameters are measured by quasi-elastic scattering of light. It is also possible to obtain the size of droplets by Transmission Electron Microscopy (TEM), by cryo-Transmission Electron Microscopy (cryoTEM) or further by Atomic Force Microscopy (AFM). Diameters of less than 20 nm and greater than 200 nm are difficult to attain in practice.

The term of «lipid» designates within the scope of this discussion, the whole of the fats or substances containing fatty acids present in fats of animal origin and in vegetable oils. These are hydrophobic or amphiphilic molecules mainly consisting of carbon, hydrogen and oxygen and having a density below that of water. The lipids may be in the solid state at room temperature (25° C.), like in waxes, or liquid like in oils.

The term of «amphiphilic» designates a molecule having a hydrophobic portion and a hydrophilic portion, for example a hydrophobic apolar portion and a hydrophilic polar portion.

The term of «phospholipid» is directed to lipids having a phosphate group, notably phosphoglycerides. Most often, phospholipids include a hydrophilic end formed by the phosphate group optionally substituted and two hydrophobic ends formed by chains of fatty acids. Among phospholipids, mention may in particular be made of phosphatidylcholine, phosphatidyl ethanolamine, phosphatidyl inositol, phosphatidyl serine and sphingomyelin.

The term of «lecithin» designates phosphatidylcholine, i.e. a lipid formed from a choline, a phosphate, a glycerol and two fatty acids. It covers more broadly phospholipids extracted from living material, of plant or animal origin, in so far that they in majority consist of phosphatidylcholine. These lecithins generally form mixtures of lecithins bearing various fatty acids.

By the term of «surfactant» are meant compounds with an amphiphilic structure which gives them particular affinity for interfaces of the oil/water and water/oil type which gives them the capability of lowering the free energy of these interfaces and of stabilizing dispersed systems.

By the term of «co-surfactant» is meant a surfactant acting in addition to a first surfactant (i.e. the amphiphilic lipid) for further lowering the energy of the interface.

By «lipophilic» agent of interest is meant an agent of interest which is in majority, preferably totally located in the dispersed phase, inside or at the surface of the droplets. A lipophilic agent of interest has affinities for oily compounds (fats, oils, waxes . . . ) and apolar solvents (toluene, hexane . . . ). The forces allowing solubilization of the lipophilic agent of interest are in majority London forces (Van der Waals interactions). A lipophilic agent of interest has a high oil/water sharing coefficient.

By «hydrophilic» agent of interest is meant an agent of interest which is in majority, preferably totally located in the continuous aqueous phase. Its solubility in water is generally greater than 1% by weight. Solubilization in water of hydrophilic agents of interest generally stems from hydrogen and/or ionic bonds between the hydrophilic agents of interest and water.

By «immunogenic composition», is meant a composition which may be administered to humans or animals in order to induce an immune response. Said immune response may be a humoral immune response, i.e. an immune response which is expressed by a production of neutralizing antibodies, or a cytotoxic cell immune response, i.e., an immune response which is expressed by activation of certain cells, notably cells exhibiting antigens (for example dendritic cells), T lymphocytes, B lymphocytes, NK (natural killer) lymphocytes.

By «antigen» («Ag» in the present application), is meant any antigen (including a specific epitope) which may be used in a vaccine, i.e. any molecule which may be specifically recognized by the cells of the immune system, such as dendritic cells, B cells, and/or T cells (Pulendran et al., *Nature Immunology*, 2011, 12, 509-517).

In certain embodiments, the antigen is a vector comprising a polynucleotide coding for an antigen polypeptide, said polynucleotide being operationally bound to one or several regulatory sequences which allow regulation of the expression of said polynucleotide.

In certain embodiments, the antigen is an allergen. Examples of allergens may be in a non-limiting way, pollen allergens (from trees, grasses, etc.), mite allergens (from domestic dust or from storage), insect allergens (hymenoptera, cockroaches, etc.), animal allergens (from dogs, cats, horses, rats, mice, etc.), fungi allergens and food allergens. The food allergens may stem from milk, eggs, vegetables (including groundnuts and soya), walnuts and hazelnuts, wheat, crustaceans, fish and shellfish and products which are derived from them. In particular, the food allergens may be ovalbumin or gluten.

In certain embodiments, the antigen used in the invention may also be derived from any living or non-living organism;

from cell fragments; from anatoxin. The antigen may also be derived from a natural or attenuated microorganism, such as a virus, a bacterium, a parasite or a yeast.

In certain embodiments, the antigen may for example be a portion of an antigen molecule, or a synthetic molecule or a molecule obtained by recombinant technologies.

In certain embodiments, the antigen is a polypeptide, a carbohydrate or a lipid.

Non-limiting examples of antigens are antigens derived:
(i) from viruses, such as antigens derived from the human immunodeficiency virus of type 1 or 2 (HIV for «human immunodeficiency virus») (e.g. tat, nef, gp120, gp160, gp40, p24, gag, env, vif, vpr, vpu, rev); from the human herpes simplex virus of type 1 or 2 (HSV for «herpes simplex virus») (e.g. gH, gL, gM, gB, gC, gK, gE, gD, ICP27, ICP 47, IC P 4, ICP36 from HSV1 or HSV2); from the cytomegalovirus such as gB, from the Epstein Barr virus (e.g. gp350); from the chickenpox virus (e.g. gpI, II, III and 1E63); or from the virus of hepatitis A, B (e.g. the surface antigen of hepatitis B («hepatitis B surface antigen» or the nucleocapsid antigen of hepatitis («hepatitis core antigen»)); from paramyxoviruses, such as the respiratory syncytial virus, the parainfluenza virus, measles virus, or mumps virus; from papilloma viruses (e.g. HPV6, 11, 16, 18, e.g. L1, L2, E1, E2, E3, E4, E5, E6, E7); flaviviruses such as yellow fever virus, dengue virus, Saint-Louis encephalitis virus, Japanese encephalitis virus; influenza virus (e.g. the proteins HA, NP, NA, or M);
(ii) from bacteria, such as antigens derived from bacteria of the *Neisseria* genus, including *N. gonorrhea* and *N. meningitidis* (e.g. the binding proteins to transferrin, binding proteins to lactoferrin, PiIC, adhesins); of the *Streptococcus* genus, including *S. pyogenes* (e.g. M proteins, C5A protease), *S. pneumoniae* (e.g. PsaA, PspA, streptolysin, binding proteins to choline), *S. agalactiae* and *S. mutans*; of the *Haemophilus* genus, including *H. ducreyi, H. influenzae* of type B (e.g. PRP), non-typable *H. influenzae* (e.g. OMP26, high molecular weight adhesins, P5, P6, D protein, D lipoprotein, fibrin); of the *Moraxella* genus, including *M catarrhalis* (e.g. high and low molecular weight adhesins and invasins); of the *Bordetella* genus, including *B. pertussis* (e.g. pertactin, pertussic toxin, filamentous hemagglutinin, adenylate cyclase), *B. parapertussis* and *B. bronchiseptica*; of the *Mycobacterium* genus, including *M. tuberculosis* (e.g. ESAT6, antigen 85A, -B or -C, MPT 44, MPT59, MPT45, HSP10, HSP65, HSP70, HSP75, HSP90, PPD 19 kDa [Rv3763], PPD 38 kDa [Rv0934]), *M. bovis, M. leprae, M. avium, M. paratuberculosis* and *M. smegmatis*; of the *Legionella* genus, including *L. pneumophila*; of the *Escherichia* genus, including enterotoxic *E. coli* (e.g. colonization factors, thermolabile toxin or thermostable toxin), enterohaemorragic *E. coli*, enteropathogenic *E. coli* (e.g. verotoxin); of the *Vibrio* genus, including *V. cholera* (cholera toxin); of the *Shigella* genus, including *S. sonnei, S. dysenteriae* and *S. flexnerii*; of the *Yersinia* genus, including *Y. enterocolitica* (e.g. the Yop protein), *Y. pestis, Y. pseudotuberculosis*; of the *Campylobacter* genus, including *C. jejuni* (e.g. toxins, adhesins and invasins) and *C. coli*; of the *Salmonella* genus, including *S. typhi, S. paratyphi, S. choleraesuis, S. enteritidis*; of the *Listeria* genus, including *L. monocytogenes*; of the *Helicobacter* genus, including *H. pylon* (e.g. urease, catalase, vacuolar toxin); of the *Pseudomonas* genus, including *P. aeruginosa*; of the *Staphylococcus* genus, including *S. aureus, S. epidermidis*; of the *Enterococcus* genus, including *E. faecalis, E. faecium*; of the *Clostridium* genus, including *C. tetani* (e.g. tetanus toxin), *C. botulinum* (e.g. botulic toxin), *C. difficile* (e.g. toxins A and B); of the *Bacillus* genus, including *B. anthracis*; of the *Corynebacterium* genus, including *C. diphtheriae* (e.g. diphtheria toxin); of the *Borrelia* genus, including *B. burgdorferi* (e.g. OspA, OspC, DbpA, DbpB), *B. garinii* (e.g. OspA, OspC, DbpA, DbpB), *B. afzelii* (e.g. OspA, OspC, DbpA, DbpB), *B. andersonii* (e.g. OspA, OspC, DbpA, DbpB), *B. hermsii*; of the *Ehrlichia* genus, including *E. equi* and the agent of the human granulocytic Ehrlichiosis agent; of the *Rickettsia* genus, including *R. rickettsii*; of the *Chlamydia* genus, including *C. trachomatis* (e.g. MOMP, binding proteins to heparin), *C. pneumoniae* (e.g. MOMP, binding proteins to heparin), *C. psittaci*; of the *Leptospira* genus, including *L. interrogans*; of the *Treponema* genus, including *T. pallidum* (e.g. the rare proteins of the external membrane), *T. denticola, T. hyodysenteriae*;
(iii) from parasites, such as antigens derived from parasites of the *Plasmodium* genus, including *P. falciparum* (e.g. RTS, S and TRAP); of the *Toxoplasma* genus, including *T. gondii* (e.g. SAG2, SAG3, Tg34); of the *Entamoeba* genus, including *E. histolytica*; of the *Babesia* genus, including *B. microti*; of the *Trypanosoma* genus, including *T. cruzi*; of the *Giardia* genus, including *G. lamblia*; of the *Leishmania* genus, including *L. major*; of the *Pneumocystis* genus, including *P. carinii*; of the *Trichomonas* genus, including *T. vaginalis*; of the *Schisostoma* genus, including *S. mansoni*, or
(iv) from yeasts of the *Candida* genus, including *C. albicans*; of the *Cryptococcus* genus, including *C. neoformans*.

In certain embodiments, the antigen is a tumoral antigen and may be used for immunotherapeutic treatment of cancers. The tumoral antigens may derive from cancer of the prostate, of the breast, of the colon, of the lung, of the liver, of the pancreas, of the kidney, of the bladder, from a melanoma, carcinoma, sarcoma. Non-limiting examples of tumoral antigens derived from a melanoma, carcinoma (lung, bladder), or from a sarcoma are MAGE 1, 3 and MAGE 4, PRAME, BAGE, Lage, SAGE, HAGE or GAGE. Non-limiting examples of antigens derived from prostate cancer are the specific antigen of the prostate (PSA for «prostate specific antigen»), PAP, PSCA, PSMA, P501S or prostase. Non-limiting examples of antigens derived from breast cancer are Muc-1, Muc-2, EpCAM, HER2/Neu, mammaglobin. Other examples of tumoral antigens useful in the context of the present invention are Plu-1, HASH-1, HasH-2, Cripto, Criptin, tyrosinase, survivin.

In certain embodiments, the antigen comprises or consists in a fragment of at least 6, 7, 8, 10, 15, 20, 30, 40, 50, 75, 100, 150, 200, 300, 400, 500 contiguous amino acids of an antigen as defined above.

In certain embodiments, the antigen is a fusion protein comprising or consisting in at least 2 antigens or antigen fragments as defined above.

By «biological targeting ligand» is meant a molecule allowing an increase in the specific recognition of a cell or of an organ which is intended to be targeted, notably an immune cell, such as for example T lymphocytes, B lymphocytes, NK lymphocytes, dendritic cells, macrophages and promoting internalization of the droplets by the target cells. The biological targeting ligand may notably be selected from antibodies, peptides, saccharides, aptamers, oligonucleotides or compounds like folic acid.

Preferably, the biological targeting ligand gives the possibility of targeting dendritic cells. According to this embodiment, the biological targeting ligand may therefore be a mannosylated molecule, such as a mannosylated peptide or lipid, a mannose polymer, such as mannan, which may be recognized by mannose receptors present at the surface of dendritic cells, and/or an antibody, an antibody fragment or a ligand specifically recognizing dendritic cells such as anti-DC-SIGN anti-DEC-205, anti-CD-207.

By «immunostimulating agent», also called an «adjuvant», is meant a substance capable of improving, or increasing the immune response induced by the antigen as defined above. Suitable immunostimulating agents include aluminium salts, calcium, magnesium, iron or zinc salts, saponin, lipid A (also known as MPLA for «monophosphoryl lipid A») or one of its derivatives, an immunostimulating oligonucleotide, an alkyl phosphate glucosamide, cytokines, chemokines or a combination of these compounds. Examples of saponins are Quil A and of its purified fragments are QS7 and QS21. Examples of cytokines are interleukin 1 beta (IL-1β), interleukin 6 (IL-6), gamma interferon (IFN-γ), tumor necrosis factor alpha (TNF-α). Examples of chemokines are MCP-1 (monocyte chemoattractant protein 1, also known under the name of CCL-2), MIP-1 alpha (also known as CCL-3) and MIP-1 beta (also known as CCL-4).

By the term of «fatty acid» is meant the designation of aliphatic carboxylic acids having a carbon chain with at least 4 carbon atoms. Natural fatty acids have a carbon chain from 4 to 28 carbon atoms (generally an even number). A fatty acid is said to be with a long chain for a length of 14 to 22 carbons and with a very long chain if there are more than 22 carbons.

By the term of «hydrocarbon chain» is meant a chain consisting of carbon and hydrogen atoms, either saturated or unsaturated (double or triple bond). The preferred hydrocarbon chains are alkyls or alkenyls.

By the term of «alkylene» is meant a designation of a linear or branched, preferably linear saturated hydrocarbon aliphatic divalent group.

By «activated ester», is meant a group of formula —CO-LG, by «activated carbonate», is meant a group of formula —O—CO-LG, by «activated carbamate», is meant a group of formula —NH—CO-LG, wherein LG is a good leaving group notably selected from a bromine atom, a chlorine atom, an imidazolyl, a pentafluorophenolate, a pentachlorophenolate, a 2,4,5-trichlorophenolate, 2,4,6-trichlorophenolate, an —O-succinimidyl group, —O-benzotriazolyl, —O-(7-aza-benzotriazolyl) and —O-(4-nitrophenyl) groups.

The embodiments described for each of the components of the immunogenic composition may of course be combined with each other. Further, when a component consists of several radicals (for example the surfactant bearing an antigen of formula (I) consists of different radicals $L_1$-, —$X_1$—, —$H_1$—, —$Y_1$, -G-, —$Z_1$— and Ag), the different embodiments of each of the radicals may of course may be combined with each other.

Surfactant Bearing an Antigen of Formula (I)

The immunogenic composition according to the invention comprises a surfactant of formula (I) which bears an antigen. This surfactant allows covalent binding of the antigen Ag to the droplets.

The surfactant of formula (I) is located in the crown of the droplets of the emulsion, the $L_1$ group(s) being directed towards the inside of the droplets while the antigen Ag is directed towards the outside of the droplets, towards the continuous aqueous phase.

The group $X_1$ is a binding group binding the lipophilic and hydrophobic groups. The group G is a binding group between the [lipophilic-hydrophilic] portions and the antigen. The group $Y_1$ is a binding group binding the group G to the [lipophilic-hydrophilic] portions.

In an embodiment, in the aforementioned formula (I):

$L_1$ is selected from:

- a group R or R—(C═O)—, wherein R represents a linear hydrocarbon chain comprising from 7 to 23 carbon atoms, preferably from 11 to 23 carbon atoms,
- an ester or amide of fatty acids comprising from 8 to 24 carbon atoms (preferably from 12 to 24 carbon atoms) and of phosphatidylethanolamine, such as distearyl phosphatidylethanolamine (DSPE), and
- a poly(propylene oxide), and/or $X_1$, $Y_1$ and $Z_1$ are independently selected from:

- a simple bond,
- a group Z selected from —O—, —NH—, —O(OC)—, —(CO)O—, —(CO)NH—, —NH(CO)—, —O—(CO)—O—, —NH—(CO)—O—, —O—(CO)—NH— and —NH—(CO)—NH,
- a group Alk being an alkylene comprising from 1 to 8 carbon atoms, optionally comprising a ring (for example a radical

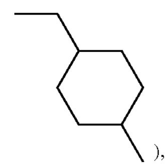

), and

- a group Z-Alk, Alk-Z, Alk-Z-Alk or Z-Alk-Z wherein Alk and Z are as defined above and wherein both groups Z of the Z-Alk-Z group are identical or different, and/or $H_1$ is selected from a poly(ethylene oxide) typically comprising from 3 to 500 ethylene oxide units, preferably from 20 to 200 ethylene oxide units, and/or G comprises at least one group G' having one of the following formulas (the $Y_1$ and $Z_1$ group(s) may be connected on the left or on the right of the formulae described below, for example, when G is a group G' of formula (XI), the surfactant of formula (I) may have the formula $L_1$-$X_1$—$H_1$—$Y_1$—CONH—$Z_1$—Ag or $L_1$-$X_1$—$H_1$—$Y_1$—NHCO—$Z_1$—Ag):

(XI)

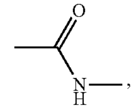

, (XII)

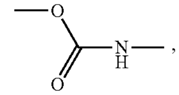

, (XIII)

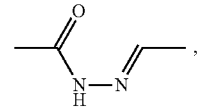

, wherein $A_{102}$ represents CH or N, $R_{102}$ represents H or a linear hydrocarbon chain comprising from 1 to 6 carbon atoms, $A_{101}$ represents —O—, —NH—(CO)— or —O—(CO)—, $R_{100}$ represents H or a methyl, $A_{100}$ represents —O— or —NH— and $R_{101}$ represents H, Me or —OMe.

By the formula is meant that the $Z_1$ group or the $Y_1$ group may be bound to any of the six atoms of the cyclooctyl group and by the formula is meant that the groups $A_{101}$ and $R_{101}$ may be bound to any of the four atoms of the phenyl group.

Notably, v represents 1 or 2, y represents preferably 1.

The group G may comprise one or several of the groups G' defined above.

Thus, in a first embodiment, the group G consists of a group G'. In this embodiment, in formula (I), v represents 1.

In a second embodiment, the group G fits the formula -G'-Y$_3$-G'- wherein:

Y$_3$ represents a binding group, notably selected from:
  a simple bond,
  a group Z selected from —O—, —NH—, —O(OC)—, —(CO)O—, —(CO)NH—, —NH(CO)—, —O—(CO)—O—, —NH—(CO)—O—, —O—(CO)—NH— and —NH—(CO)—NH,
  a group Alk being an alkylene comprising from 1 to 6 carbon atoms, and
  a group Z-Alk, Alk-Z, Alk-Z-Alk or Z-Alk-Z wherein Alk and Z are as defined above and wherein both groups Z of the Z-Alk-Z group are identical or different.

each of the G's independently represent a group of formulae (XI) to (XXVI), mentioned above, and preferably, both groups G' of the formula -G'-Y$_3$-G'- are identical.

This embodiment is particularly of interest when both groups G' are identical and comprise a cleavable function. Indeed, it is then sufficient to cleave a single one of the two functions in order to break the covalent bonds between the droplets of the immunogenic composition and the antigen, which improves the probabilities of success of the cleaving and therefore the release of the antigen out of the droplets after cell capture.

When $L_1$ represents a group R—(C=O)—, wherein R represents a linear hydrocarbon chain comprising from 7 to 23 carbon atoms, $L_1$ represents a group derived from a fatty acid comprising from 8 to 24 carbon atoms.

By «$L_1$ represents an ester or an amide of fatty acids comprising from 8 to 24 carbon atoms and of phosphatidylethanolamine», is meant that it represents a group of formula:

wherein

R$_3$ and R$_4$ represent independently a linear hydrocarbon chain comprising from 7 to 23 carbon atoms, preferably from 11 to 23 carbon atoms, A$_3$ and A$_4$ represent O or NH, and M represents H or a cation.

In an embodiment, in the aforementioned formula (I), the radical $L_1$-$X_1$—$H_1$— consists in one of the groups of the following formulae (the radical —$Y_1$-G-$Z_1$—Ag being bound on the right side of the formulae described below):

(CI)

(CII)

(CIII)

(CIV)

wherein:

R$_1$, R$_2$, R$_3$ and R$_4$ independently represent a linear hydrocarbon chain comprising from 7 to 23 carbon atoms, preferably from 11 to 23 carbon atoms, A$_1$, A$_2$, A$_3$ and A$_4$ represent O or NH, m, n, o and p independently represent integers from 3 to 500, preferably 20 to 200, and a represents an integer from 20 to 120, M represents H or a cation.

The radical $L_1$-$X_1$—$H_1$— of formula (CII) is preferred. Indeed, it is easy to prepare (notably by forming an ester or an amide between a fatty acid and a derivative of poly (ethylene glycol)).

The radical $L_1$-$X_1$—$H_1$— of formula (CII) with A$_2$ representing NH are more preferred, since the surfactants comprising such radicals give the possibility of avoiding the leaking of lipophilic agents of interest and/or target ligand and/or immunostimulating agent optionally present, out of the droplets of the immunogenic composition, more efficiently than surfactants comprising a radical $L_1$-$X_1$—$H_1$— of formula (CII) with A$_2$ representing O.

In an embodiment, in formula (I):

v represents 1, $L_1$ is R—(C=O)—, wherein R represents a linear hydrocarbon chain comprising from 7 to 23 carbon atoms, preferably from 11 to 23 carbon atoms, H$_1$ is a poly(ethylene oxide) comprising from 3 to 500 ethylene oxide units, X$_1$ represents —O— or —NH—, G consists of a group G' of formula (XIV) wherein A$_{102}$ represents N, Y$_1$ represents —CH$_2$—CH$_2$—NH—CO—CH$_2$—CH$_2$— (a group Alk-Z-Alk above with Alk representing —CH$_2$—CH$_2$— and Z representing —NH—(CO)—) and Z$_1$ representing (a group Alk-Z above with Alk representing and Z representing (CO)), and the surfactant of formula (I) of the immunogenic composition then has the following formula (I'):

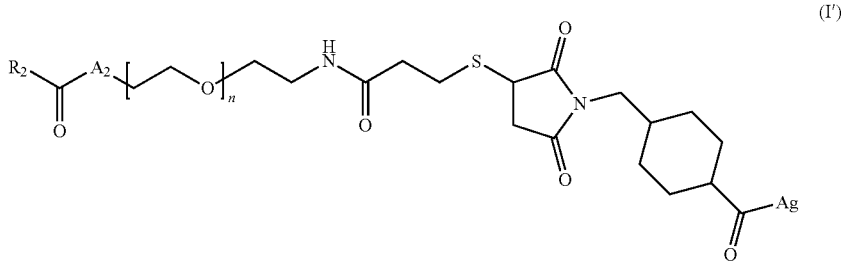

(I')

wherein:
R$_2$ represents a linear hydrocarbon chain comprising from 7 to 23 carbon atoms, notably from 11 to 23 carbon atoms, preferably 17 carbon atoms,
A$_2$ represents O or NH, preferably NH, and
n represents an integer from 3 to 500, preferably from 20 to 200, notably 100,
Ag represents an antigen.

In an embodiment, the group H$_1$ is selected from a poly(ethylene oxide) comprising more than 3 poly(ethylene oxide) units, or even more than 20 units, notably more than 50 (in the aforementioned formulae, m, n, o or p are preferably greater than 3, or even 20, notably more than 50).

In an embodiment, the group G of the surfactant of formula (I) of the immunogenic composition comprises a cleavable function, notably chemically cleavable, (when the surfactant of formula (I) is put into contact with a chemical compound capable of electrochemically cleaving the function of the G group) at certain pH's (basic or acid pH), by enzymes, by light (visible light, ultraviolet or infrared light) and/or beyond certain temperatures. Generally, the group G then comprises a group G' comprising a cleavable function.

This embodiment is of interest since it may allow delivery of the antigen Ag localized at the desired location where the chemical, electrochemical, pH or temperature stimulus occurs. For example, it is possible to deliver the antigen in the intracellular compartment of the target cells when the antigen is bound to the droplet through a dithiol bond (—S—S—) (i.e. when the group G comprises at least one group G' comprising a group (XV)). Once it is phagocytosed, the particle bearing an antigen is found in the endosome where the bond (—S—S—) will be reduced by gluthathione. The free antigen may then escape from the endosome towards the cytosol so as to be subject there to crossed presentation, this is then referred to as endosomal escape (Joffre et al., Nature Reviews Immunology 2012, 12, 557-569).

For example:

the β-ketoaminoester function of the group G' of formula (XX) is cleavable at an acid pH (typically around 5), the disulfide function of the group G' of formula (XV) is cleavable with ultraviolet radiations, electrochemically, chemically (for example by contacting a reducing agent, such as tris(2-carboxyethyl)phosphine (TCEP) or dithiothreitol (DTT)), or by enzymes such as thioreductases, the amide function of the group G' of formula (XI) is cleavable by enzymes such as proteases, the phosphate function of the group G' of formula (XXII) is cleavable by enzymes such as phosphatases, the imine function of the groups G' of formulae (XXI) and (XIII) are cleavable at an acid pH or beyond certain temperatures, the cyclohexene ring of the group G' of formula (XVII) is cleavable beyond certain temperatures (by a retro Diels-Alder reaction), the carbonate function of the group G' of formula (XIX) and the carbamate function of the group G of formula (XII) are cleavable at an acid pH or chemically (for example by reaction with a nucleophilic agent), the orthonitrobenzyl function of the group G' of formula (XXIV) is cleavable under the action of light at 365 nm.

One skilled in the art, considering his/her general knowledge, is aware of the functions which are cleavable and under which conditions. He/she is notably capable of selecting the function of the group G' of the surfactant of formula (I) so that it is cleavable under the conditions encountered in the desired application of the immunogenic composition according to the invention.

In an embodiment, the immunogenic composition according to the invention comprises several surfactants of formula (I) (for example two surfactants of formula (I)), each of the surfactants of formula (I) being a bearer of an antigen of different nature. Certain biological uses may actually require administration of several antigens at the same time.

Amphiphilic Lipid

The immunogenic composition comprises an amphiphilic lipid as a surfactant which allows formation of the droplets of the dispersed phase. The amphiphilic nature of the surfactant ensures stabilization of the oil droplets within the aqueous continuous phase.

Amphiphilic lipids include a hydrophilic portion and a lipophilic portion. They are generally selected from compounds for which the lipophilic portion comprises a linear or branched, saturated or unsaturated chain, having from 8 to 30 carbon atoms. They may be selected from phospholipids, cholesterols, lysolipids, sphingomyelins, tocopherols (not esterified), glucolipids, stearylamines, cardiolipins of natural or synthetic origin; molecules consisting of a fatty acid coupled with a hydrophilic group through an ether or ester function such as sorbitan esters like for example sorbitan monooleate and monolaurate marketed under the names of Span® by Sigma; polymerized lipids; lipids conjugate with short polyethylene oxide (PEG) chains as well as non-ionic surfactants marketed under the trade names of Tween® by ICI Americas, Inc. and Triton® by Union Carbide Corp.; sugar esters such as mono- and di-laurate, mono- and di-palmitate, mono- and distearate of saccharose; said surfactants may be used alone or as mixtures.

The phospholipids are particularly preferred amphiphilic lipids, notably the phospholipids selected from phosphatidylcholine, phosphatidylethanolamine, phosphatidylserine, phosphatidylglycerol, phosphatidylinositol, phosphatidyl-phosphatidic acid, either non-hydrogenated or hydrogenated, notably marketed by Lipoid.

Lecithin is the preferred amphiphilic lipid.

Generally, the dispersed phase includes from 0.01 to 99% by weight, preferably from 5 to 75% by weight, in particular from 5 to 60% and most particularly from 5 to 45% by weight of amphiphilic lipid.

The amount of amphiphilic lipid advantageously contributes to controlling the size of the droplets of the dispersed phase of the immunogenic composition.

Solubilizing Lipid

The immunogenic composition comprises a solubilizing lipid, which notably allows:
- an increase in the physicochemical stability of the immunogenic composition, and
- when the immunogenic composition comprises a lipophilic agent of interest and/or a targeting ligand and/or an immunostimulating agent encapsulated in the droplets:
  - solubilization of the lipophilic agent of interest and/or the target ligand and/or the immunostimulating agent, and
  - improvement in the control of the desalting of the lipophilic agent of interest and/or of the target ligand and/or of the immunostimulating agent.

Preferably, the solubilizing lipid is solid at room temperature (20° C.).

The solubilizing lipid may notably consist of derivatives of glycerol, and in particular of glycerides obtained by esterification of the glycerol with fatty acids, notably in the case when the amphiphilic lipid is a phospholipid.

The preferred solubilizing lipids, in particular for the phospholipids, are glycerides of fatty acids, notably of saturated fatty acids, and in particular of saturated fatty acids including 8 to 18 carbon atoms, still preferably 12 to 18 carbon atoms. Advantageously, the solubilizing lipid consists of a complex mixture of different glycerides. By "complex mixture", is meant a mixture of mono-, di- and tri-glycerides, comprising fatty chains of different lengths, said lengths preferably extending from C8 to C18, for example, in an association, C8, C10, C12, C14, C16 and C18 chains, or from C10 to C18, for example comprising as an association, C10, C12, C14, C16 and C18 chains.

According to an embodiment, said fatty chains may contain one or several unsaturations.

Preferably, the solubilizing lipid consists of a mixture of saturated fatty acids glycerides including at least 10% by weight of C12 fatty acids, at least 5% by weight of C14 fatty acids, at least 5% by weight of C16 fatty acids and at least 5% by weight of C18 fatty acids.

Preferably, the solubilizing lipid consists of a mixture of glycerides of saturated fatty acids including 0% to 20% by weight of C8 fatty acids, 0% to 20% by weight of C10 fatty acids, 10% to 70% by weight of C12 fatty acids, 5% to 30% by weight of C14 fatty acids, 5% to 30% by weight of C16 fatty acids and 5% to 30% by weight of C18 fatty acids.

The mixtures of solid semi-synthetic glycerides at room temperature marketed under the trade name of Suppocire®NB by Gattefossé and approved for use in humans are particularly preferred solubilizing lipids. The Suppocire® of type N are obtained by direct esterification of fatty acids and of glycerol. These are hemi-synthetic glycerides of saturated C8-C18 fatty acids, for which the qualitative-quantitative composition is indicated in Table 1 below.

TABLE 1

| Fatty acid composition of Suppocire ® NB from Gattefossé | |
|---|---|
| Chain length | [% by weight] |
| C8 | 0.1 to 0.9 |
| C10 | 0.1 to 0.9 |
| C12 | 25 to 50 |
| C14 | 10 to 24.9 |
| C16 | 10 to 24.9 |
| C18 | 10 to 24.9 |

The aforementioned solubilizing lipids give the possibility of obtaining an advantageously stable immunogenic composition. Without intending to be bound to a particular theory, it is assumed that the aforementioned solubilizing lipids give the possibility of obtaining in the immunogenic composition droplets having an amorphous core. The thereby obtained core has a high internal viscosity without however exhibiting crystallinity. Now, crystallization is detrimental for the stability of the immunogenic composition since it generally leads to aggregation of the droplets and/or to an expulsion of the lipophilic agent of interest and/or of the target ligand and/or of the immunostimulating agent, if present, outside the droplets. These physical properties promote physical stability of the immunogenic composition.

The amount of solubilizing lipid may widely vary depending on the nature and on the amount of amphiphilic lipid present in the dispersed phase. Generally, the dispersed phase includes from 1 to 99% by weight, preferably from 5 to 80% by weight and most particularly from 30 to 75% by weight of solubilizing lipid.

Co-Surfactant

The immunogenic composition according to the invention comprises a co-surfactant. This co-surfactant is partly located in the continuous aqueous phase and partly in the droplets of the dispersed phase.

Preferably, the co-surfactant includes at least one chain consisting of ethylene oxide or ethylene oxide and propylene oxide units. It may in particular be selected from conjugate compounds polyethyleneglycol/phosphatidyl-ethanolamine (PEG-PE), ethers of fatty acid and of polyethyleneglycol, esters of fatty acid and of polyethyleneglycol and block copolymers of ethylene oxide and propylene oxide.

The polyalkoxylated chain of the co-surfactant preferably comprises from 10 to 200, typically from 10 to 150, notably from 20 to 100 ethylene oxide/propylene oxide units.

As an example of co-surfactants, mention may in particular be made of conjugate compounds based on polyethyleneglycol/phosphatidyl-ethanolamine (PEG-PE), ethers of fatty acid and of polyethyleneglycol such as the products marketed under the trade names of Brij® (for example Brij® 35, 58, 78 or 98) by ICI Americas Inc., esters of fatty acid and of polyethyleneglycol such as the products marketed under the trade names Myrj® by ICI Americas Inc. (for example Myrj® s20, s40 or s100, formerly designated as 49, 52 or 59) and block copolymers of ethylene oxide and propylene oxide such as the products marketed under the trade names of Pluronic® by BASF AG (for example Pluronic® F68, F127, L64, L61, 10R4, 17R2, 17R4, 25R2 or 25R4) or the products marketed under the trade name Synperonic® by Unichema Chemie BV (for example Synperonic® PE/F68, PE/L61 or PE/L64).

In the immunogenic composition according to the invention, the molar ratio of the surfactant bearing an antigen of formula (I) over the sum of the co-surfactant and of the surfactant bearing an antigen of formula (I) is from 0.01 to 5%, notably from 0.1 to 3%.

Indeed, below 0.01%, and sometimes below 0.1%, the amount of antigen is too small for the applications of the composition as explained hereafter.

Beyond 5%, and sometimes beyond 3%, the immunogenic composition is difficult to prepare and/or is not very stable. Indeed, as explained hereafter, the preparation of the immunogenic composition requires a premixed emulsion comprising a surfactant (LI) comprising a functionalizable group $G_1$. In order to obtain an immunogenic composition in which said ratio is greater than 5%, it is necessary to prepare a premixed emulsion in which the molar ratio of the surfactant of formula (LI) over the sum of the co-surfactant and of the surfactant of formula (LI) is greater than 5%, which is difficult. Indeed, the droplets of such an emulsion have too great surface density of functionalizable group $G_1$ and the emulsion is therefore not very stable. Further, subsequent grafting of the antigen on the premixed emulsion is difficult. Indeed it was not possible to formulate emulsions for molar proportions of surfactant bearing an antigen of formula (I) over the sum of the co-surfactant and of the surfactant bearing an antigen of formula (I) of more than 5%.

Generally, the dispersed phase includes from 0.01 to 3% by weight, preferably from 0.1 to 1.3% by weight and most particularly from 0.2 to 0.7% by weight of co-surfactant.

Generally, the mass fraction of amphiphilic lipid with respect to the weight of co-surfactant is from 0.005% to 100%, notably from 0.01% to 50%, preferably from 0.1% to 30%. Indeed, below 0.005% and beyond 100%, the droplets of the dispersed phase are often not sufficiently stable and coalesce in a few hours and it is often difficult to obtain droplets with a diameter of less than 200 nm.

Generally, the immunogenic composition does not include any additional surfactants: the only surfactants of the immunogenic composition are the amphiphilic lipid, the co-surfactant, the surfactant of formula (I) and the optional cationic surfactant.

In an embodiment, a proportion (100−x) %, wherein 0<x<100, of the co-surfactant is covalently grafted to a biological target ligand.

The immunogenic composition according to the invention always comprises a non-zero x proportion of «free» co-surfactant (not including any grafted biological target ligand). The co-surfactant consists of x % of «free» co-surfactant and of (100−x) % of co-surfactant on which is grafted a biological targeting ligand. In this embodiment, by «the molar ratio of the surfactant bearing an antigen of formula (I) over the sum of the co-surfactant and of the surfactant bearing an antigen of formula (I) is from 0.01 to 5%», is meant that the molar ratio of the surfactant bearing an antigen of formula (I) over the sum of the «free» co-surfactant and of the surfactant bearing an antigen of formula (I) is from 0.01 to 5%, i.e. the molar ratio of the surfactant bearing an antigen of formula (I) over the sum of x % of the co-surfactant, and of the surfactant bearing an antigen of formula (I) is from 0.01 to 5%

Typically, the biological targeting ligand was grafted through a covalent bond to the co-surfactant as defined above. The grafting may be carried out before or after the formation of the emulsion used for preparing the immunogenic composition (premix emulsion hereafter). The latter case may be recommended when the chemical reactions used are compatible with the stability of the emulsions, notably in terms of pH. Preferably, the pH during the grafting reaction is comprised between 5 and 11.

Generally, this grafting was carried out at one end of the polyalkoxylated chains of the co-surfactant, and the biological targeting ligand is thus located at the surface of the droplets of the dispersed phase of the immunogenic composition.

Immunostimulating Agent

In an embodiment, the immunogenic composition may further comprise an immunostimulating agent, which allows improvement or increase in the immune response.

The immunostimulating agent is notably selected from an aluminium salt, a calcium, magnesium, iron or zinc salt, saponin (e.g. Quil A and its purified fragments such as QS7 and QS21), the lipid A or one of its derivatives, an immunostimulating oligonucleotide, an alkyl phosphate glucosamide. Preferably, the immunostimulating agent is the lipid A.

The proportion of immunostimulating agent in the dispersed phase depends on the nature and of the efficiency of the immunostimulating agent and on the presence or not of a biological targeting ligand in the immunogenic composition. This proportion may easily be determined by one skilled in the art.

Biological Target Ligand

In an embodiment, the immunogenic composition may comprise a biological target ligand.

The biological targeting ligand may either be grafted or not on the co-surfactant, i.e.:
  in free form in the droplets, i.e. it is encapsulated in the droplets, either in the crown if it has an amphiphilic nature, or in the core if it has a lipophilic nature, and/or
  in a form covalently grafted to the co-surfactant, as explained above.

In certain embodiments, the biological targeting ligand is a mannosylated lipid or an anti-DC-sign antibody.

The proportion of biological targeting ligand in the dispersed phase depends on the nature and on the efficiency of the biological target ligand. This proportion may easily be determined by one skilled in the art.

Agent of Interest

In an embodiment, the immunogenic composition may comprise one or several agents of interest.

The agent of interest may be of a very diverse nature. Thus, the agent of interest may be:
  an optical agent such as a coloring agent, a chromophore, a fluorophore, for example 1,1'-dioctadecyl 3,3,3',3'-tetramethylindodicarbocyanine perchlorate (DiD), 1,1'-dioctadecyl 3,3,3',3'-tetramethylindotricarbocyanine iodide (DiR), indocyanine green (ICG), or further components having optoelectronic properties, such as optical saturation agents or absorbants,
  a physical agent, such as a radioactive isotope or a photo-sensitizer,
  an imaging agent, notably for MRI (Magnetic Resonance Imaging), PET (Positron Emission Tomography), SPECT (Single Photon Emission Computed Tomography), ultrasonic echography, radiography, X tomography and optical imaging (fluorescence, bioluminescence, scattering . . . ). These agents may give the possibility of tracking the position of the droplets (and therefore of the antigen) after administering the immunogenic composition to the patient, and/or
  a therapeutic agent, notably selected from an antibiotic, an anticancer agent, an antiviral agent, an antiparasite agent, a therapeutic protein (such as a cytokine or a chemokine) and a mixture thereof.

The amounts of agents of interest depend on the targeted application as well as on the nature of the agents.

When the immunogenic composition according to the invention comprises an agent of interest, it most often contains an amount from 0.001 to 30% by weight, preferably 0.01 to 20% by weight, and still preferably 0.1 to 10% by weight of agent of interest.

The agent of interest may be hydrophilic (it is then located in the continuous aqueous phase of the immunogenic composition) or lipophilic (it is then encapsulated in the droplets forming the dispersed phase of the immunogenic composition or is located in the crown of the droplets, according to its lipophilic or amphiphilic affinity).

Cationic Surfactant

The formulation according to the invention may comprise a cationic surfactant, notably selected from:

N[1-(2,3-dioleyloxy)propyl]-N,N,N-trimethylammonium (DOTMA), 1,2-dioleyl-3-trimethylammonium-propane (DOTAP), N-(2-hydroxyethyl)-N,N-dimethyl-2,3-bis(tetradecyloxy-1-propananium) (DMRIE), 1-[2-(oleoyloxy)ethyl]-2-oleyl-3-(2-hydroxyethyl)imidazolinium (DOTIM), and dioctadecylamidoglycylspermin (DOGS) (in a protonated form), and preferably being 1,2-dioleyl-3-trimethylammonium-propane (DOTAP).

The cationic surfactant is located in the crown of the droplets of the formulation. The cationic surfactant notably allows improvement, or acceleration of the capture of the droplets by the immune cells. The cationic surfactant also has the effect of producing at the administration site a slight local inflammation which attracts the immune cells on the administration site of the droplets, thereby allowing an acceleration of the capture of the droplets by the immune cells (Doroud et al./Journal of Controlled Release 153 (2011) 154-162).

Generally, the dispersed phase includes from 0 to 25% by weight, preferably from 0 to 7% by weight of cationic surfactant. These proportions are particularly adapted for improving, or accelerating the capture of the droplets by the immune cells.

Oil

The dispersed phase of the immunogenic composition according to the invention may also include one or several oils.

The oils used preferably have a hydrophilic-lipophilic balance (HLB) of less than 10 and still more preferably from 3 to 9. Advantageously, the oils are used without any chemical or physical modification prior to the formation of the immunogenic composition.

According to the contemplated applications, the oils may be selected from biocompatible oils, and in particular from oils of natural origin (vegetable or animal) or of synthetic origin. Among such oils, mention may notably be made of oils of vegetable natural origin among which notably appear soya, flax, palm, groundnut, olive, sesame, grape pip and sunflower oils; the synthetic oils among which notably appear triglycerides, diglycerides and monoglycerides; and oils stemming from animal fats. These oils may be first pressed, refined or inter-esterified.

The preferred oil is soya oil.

Generally, if present, the oil is contained in the dispersed phase in a proportion ranging from 1 to 80% by weight, preferably from 5 to 50% by weight and most particularly from 10 to 30% by weight based on the total weight of the dispersed phase.

Aqueous Phase

The continuous aqueous phase of the immunogenic composition according to the invention preferably consists of water and/or of a buffer such as a phosphate buffer like for example PBS («phosphate buffer saline») or of a saline solution, notably of sodium chloride. Generally the pH of the aqueous phase is of the order of physiological pH.

According to an embodiment, the continuous phase also includes a thickener such as glycerol, a saccharide, oligosaccharide or polysaccharide, a gum or further a protein, preferably glycerol. Indeed, the use of a continuous phase with a higher viscosity facilitates emulsification and consequently allows reduction in the sonication time.

The aqueous phase advantageously includes from 0 to 50% by weight, preferably from 1 to 30% by weight and most particularly from 5 to 20% by weight of thickener.

Of course, the aqueous phase may further contain other additives such as coloring agents, stabilizers and preservatives in a suitable amount.

Immunogenic Composition as a Gel

In an embodiment, the viscosity of the immunogenic composition is greater than 1 poise (0.1 Pa·s) at 25° C.

In this embodiment, the immunogenic composition appears as a «gel». By the term of «gel» is usually meant a thermodynamically stable solid-liquid biphasic system, consisting of a double three-dimensional continuous interpenetrated network, one solid and the second liquid. Such a gel is a liquid-solid biphasic system, the solid network of which retains a liquid phase. Although gels may be considered as solids, they have properties specific to solids (structural rigidity, elasticity upon deformation) as to liquids (vapour pressure, compressibility and electric conductivity). The interactions between the droplets may be due to Van der Waals forces, electrostatic bonds, hydrogen bonds or covalent bonds.

In the case of a nanoemulsion as a gel, the three-dimensional network is formed by the droplets, the interstices between droplets being filled with continuous phase. The bonds between the units of the network, i.e. the droplets, mainly rely on electrostatic interactions (pairs of ions). These electrostatic interactions mainly exist between nucleotide sequences which may modulate endogenic mechanisms of RNA interference and the cationic surfactants of adjacent droplets.

A nanoemulsion as a gel therefore exhibits resistance to pressure and is capable of maintaining a defined shape, which may be advantageous depending on the desired administration form and/or route.

In order to demonstrate that the immunogenic composition is in gel form, it is possible to conduct rheological studies allowing evaluation of the viscoelastic properties, and/or more structural studies showing the bonds between the droplets forming the three-dimensional network (x-ray, neutron diffraction . . . ). Indeed, a nanoemulsion as a gel has a viscosity and a larger elasticity coefficient than a liquid nanoemulsion. The nanoemulsion as a gel may, depending on the concentration of droplets and therefore on the mass fraction in the dispersed phase, be found in the viscous liquid state, in the viscoelastic solid state or elastic solid state. As compared with the aqueous dispersing phase, for which the viscosity is close to that of water (1 mPa·s at 25° C.), the nanoemulsion is considered as a viscous liquid when its viscosity is 10 times greater than that of water, i.e. >10 mPa·s at 25° C. Moreover, when it is proceeded with rheological measurement of the G' moduli (shear conservation modulus) and of the G" moduli (shear loss modulus), it is considered that the nanoemulsion is in the form of a viscous liquid when G">G'. When G' becomes close to G", the nanoemulsion is in the viscoelastic solid state. When G"<G', it is in the elastic solid state. In this embodiment, the nanoemulsion preferably appears in the viscous liquid, viscoelastic solid or solid state. The viscosity and the elasticity coefficient may be measured by a cone-plane rheometer or by a Couette rheometer. The viscosity of a liquid nanoemulsion is generally less than 1 poise, or even often less than 0.01 poise. The nanoemulsion used in this embodiment of the invention generally has a viscosity of more than 1 poise, and may have a viscosity ranging up to that of a solid (more than 1,000 poises). Structural studies, notably x-ray or neutron diffractions, also allow differentiation of the organisation of a liquid nanoemulsion, from the organization of a nanoemulsion as a gel. Indeed, the peaks of the diffractogram obtained by a liquid nanoemulsion are characteristic of the structure of the droplets of the dispersed phase (large diffraction angles characteristic of short distances), while the peaks of the diffractogram of a nanoemulsion as a gel are not only characteristic of the structure of the droplets (large diffraction angles being characteristic of short distances) but also of the organization of these droplets in a three-dimensional network (low diffraction angles being characteristic of larger distances).

The immunogenic composition as a gel is advantageously in the form of a dispersible gel, i.e. the droplets forming the three-dimensional network may be desalted in the continuous phase under certain conditions by «degelling» of the gel system, also called «disaggregation» in the present application. The disaggregation is observed by adding continuous phase to the gel, by contacting with physiological fluids upon administration of the nanoemulsion or by increasing the temperature. Indeed, adding the continuous phase causes an osmotic pressure difference between the inside of the gel and the continuous phase. The system will therefore tend to decrease, as far as cancel, this osmotic pressure difference by releasing the droplets in the excess of continuous phase, until a homogenous droplet concentration is obtained in the whole of the volume of continuous phase. The contacting with physiological fluids may also induce a chemical reaction (example: cleavage of covalent bonds of the disulfide bridge or peptide bond type, and thus release the droplets). Also, sufficiently increasing the temperature of the system amounts to giving to the different droplets thermal energy greater than the energies in play in the bonds, for example the hydrogen bonds, and thus to breaking these bonds and releasing the droplets of the three-dimensional network. These temperatures depend on the composition of the gel and more particularly on the size of the droplets and on the length of the polyalkoxylated chains of the co-surfactant. The disaggregation of the nanoemulsion as a gel may be tracked by x-ray diffraction, by differential scanning calorimetry (DSC) or by nuclear magnetic resonance (NMR).

Localization of the Components of the Droplets

As illustrated in FIG. 1, the droplets of the immunogenic composition according to the invention are organized in the form of a core-crown, wherein:
the core comprises:
the solubilizing lipid,
the optional oil,
the optional lipophilic agent of interest,
the optional lipophilic immunostimulating agent,
the crown comprises:
the amphiphilic lipid,
the surfactant bearing an antigen of formula (I),
the optional cationic surfactant,
the co-surfactant (for which a proportion (1−x) % is optionally grafted with a target ligand),
the optional biological amphiphilic target ligand,
the nucleotide sequence capable of modulating endogenous mechanisms of RNA interference,
the optional amphiphilic immunostimulating agent,
the optional amphiphilic agent of interest.

Other Properties of the Immunogenic Composition

By its formulation, the immunogenic composition according to the invention is stable and has excellent stability upon storage (of more than 5 months or even more than 8 months). In particular, because the antigen is covalently bound to the droplets, it does not migrate in the continuous aqueous phase, unlike immunogenic compositions in which the antigen is simply encapsulated.

The antigen grafted to the droplets is also stabilized by the immunogenic composition, because the co-surfactants and amphiphilic lipids protect it.

The polyalkoxylated chains of the co-surfactant and of the surfactant of formula (I), hydrated and not charged, covering the surface of the droplets, shield the charges brought by the amphiphilic lipids to the solid surface of the droplets. Therefore one is in the case of steric stabilization of the droplets and not electrostatic stabilization.

[Preparation Method]

According to a second object, the invention relates to a method for preparing the immunogenic composition as defined above, comprising the putting into contact:
of a premix emulsion comprising a continuous aqueous phase and a phase dispersed as droplets, comprising an amphiphilic lipid, a solubilizing lipid comprising at least one fatty acid glyceride, one co-surfactant comprising at least one chain consisting of alkylene oxide units and a surfactant of the following formula (LI):

$$L_1\text{-}X_1\text{—}H_1\text{—}Y_1\text{-}G_1 \quad (LI),$$

wherein the molar ratio of the surfactant of formula (LI) over the sum of the co-surfactant and of the surfactant of formula (LI) is from 0.01% to 5%,
with a compound of the following formula (LII):

$$G_2\text{-}Z_1\text{—}Ag \quad (LII)$$

wherein $L_1$, $X_1$, $H_1$, $Y_1$, $Z_1$ and Ag are as defined above, and $G_1$ and $G_2$ are groups which may react together in order to form the group G as defined above,
under conditions allowing the reaction of the surfactant of formulae (LI) with the compound of formula (LII) in order to form the surfactant bearing an antigen of formula (I) as defined above.

When the group G comprises a single group G', the groups $G_1$ and $G_2$ are typically groups which may react with each other in order to form the group G.

When the group G comprises several groups G', the premix emulsion and the compound of formula (LII) are generally put into contact with a compound which may react with them in order to form the group G. This compound typically comprises at least v $G'_1$ functions capable of reacting with the group $G_1$ and a function $G'_2$ which may react with the group $G_2$.

Thus, in the embodiment in which the group G fits the formula -G'-$Y_3$-G'- defined above, the method for preparing the immunogenic composition typically comprises the putting into contact:
of a premix emulsion as defined above,
and of the compound of formula (LII) as defined above,
with a compound of formula $G'_1$-$Y_3$-$G'_2$ wherein $Y_3$ is as defined above, $G'_1$ is a group which may react with $G_1$ in order to form the first group G' as defined above and $G'_2$ is a group which may react with $G_2$ in order to form the second group G' as defined above (of identical nature or different nature from the first group G'), under conditions allowing reaction of the surfactant of formula (LI) and of the compound of formula (LII) with the compound of formula $G'_1$-$Y_3$-$G'_2$ in order to form the surfactant bearing an antigen of formula (I) in which the group G fits the formula -G'-$Y_3$-G'- defined above.

Formation of the Surfactant Bearing an Antigen of Formula (I) by Reaction Between the Surfactant of Formula (LI) and the Compound of Formula (LII)

The premix emulsion comprises a surfactant of formula (LI) comprising a functionalizable group $G_1$, which is located at the surface of the droplets.

Advantageously, a same premix emulsion may be used for grafting antibodies of different natures, from the moment that the compound of formula (LII) comprises a group $G_2$ which may react with the group $G_1$ of the premix emulsion. It is not necessary to adapt the components of the premix emulsion and the grafting conditions for each different antigen used. Thus, the method for preparing the immunogenic composition may be applied industrially and be automated.

The formation of the surfactant bearing an antigen of formula (I) by reaction between the surfactant of formula (LI) and the compound of formula (LII) allows grafting by covalently bonding the antigen Ag to the droplets of the premix emulsion comprising the functionalizable surfactant of formula (LI). The antigen is bound to the droplets of the emulsion through a covalent bond. The grafting of the antibody to the droplets of the premix emulsion is advantageously independent of the hydrophilic, amphiphilic or lipophilic nature of the antigen. Any type of antigen may therefore be grafted, which is an advantage as compared with the immunogenic compositions based on an emulsion and on solid lipid nanoparticles of the prior art wherein the antigen is encapsulated in the droplets (the encapsulation only being possible for amphiphilic or lipophilic antigens).

Considering his/her general knowledge in chemistry, one skilled in the art is able to select the nature of the groups $G'_1$, $G'_2$, $Y_3$, $G_1$ and $G_2$ to be used in order to form the group G and the conditions allowing the reaction. Usual organic chemistry reactions may be followed, notably those described in «Comprehensive Organic Transformations: A Guide to Functional Group Preparations» of Richard C. Larock edited by John Wiley & Sons Inc, and the references which are quoted therein. Thus, the examples of groups $G_1$ and $G_2$ below are mentioned as an illustration and not as a limitation.

Typically, when the group G consists of a group G', the group $G_1$ of the surfactant of formula (LI) and the group $G_2$ of the compound of formula (LII) may for example be selected as follows:
  one of the $G_1$ and $G_2$ represents a thiol (—SH) and the other $G_1$ or $G_2$ represents:
    either a maleimide, a surfactant of formula (I) wherein G comprises a group G' representing a group of formula (XIV) wherein $A_{102}$ represents N then being formed, the contacting of the premix emulsion and of the compound of formula (LII) being preferably carried out at a temperature from 0° C. to 15° C., notably from 0 to 10° C., preferably from 0 to 5° C.,
    or a vinylsulfone, a surfactant of formula (I) wherein G comprises a group G' representing a group of formula (XVI) then being formed,
    or a group —S—S-pyridinyl or —SH, a surfactant of formula (I) wherein G comprises a group G' representing a group of formula (XV) then being formed,
  one of the $G_1$ and $G_2$ represents a hydroxyl and the other one $G_1$ or $G_2$ represents —COOH or an activated ester, a surfactant of formula (I) wherein G comprises a group G' representing a group of formula (XXIII) then being formed,
  one of the $G_1$ and $G_2$ represents an amine —$NH_2$ and the other one $G_1$ or $G_2$ represents —COOH or an activated ester, a surfactant of formula (I) wherein G comprises a group G' representing a group of formula (XI) then being formed,
  one of the $G_1$ and $G_2$ represents a hydroxyl and the other one $G_1$ or $G_2$ represents an activated carbonate or an activated carbamate, a surfactant of formula (I) wherein G comprises a group G' representing a group of formula (XIX) then being formed,
  one of the $G_1$ and $G_2$ represents an amine —$NH_2$ and the other one $G_1$ or $G_2$ represents an activated carbonate or an activated carbamate, a surfactant of formula (I) wherein G comprises a group G' representing a group of formula (XII) then being formed,
  one of the $G_1$ and $G_2$ represents an amine —$NH_2$ and the other one $G_1$ or $G_2$ represents an aldehyde —CHO, a surfactant of formula (I) wherein G comprises a group G' representing a group of formula (XXI) then being formed,
  one of the $G_1$ and $G_2$ represents a hydrazide of formula —(C=O)—NH—$NH_2$ and the other one $G_1$ or $G_2$ represents a group —(C=O)—$R_{102}$, a surfactant of formula (I) wherein G comprises a group G' representing a group of formula (XIII) then being formed,
  one of the $G_1$ and $G_2$ represents an alkyne and the other one $G_1$ or $G_2$ represents an azide, a surfactant of formula (I) wherein G comprises a group G' representing a group of formula (XVIII) then being formed,
  one of the $G_1$ and $G_2$ represents a cyclooctyne and the other one $G_1$ or $G_2$ represents an azide, a surfactant of formula (I) wherein G comprises a group G' representing a group of formula (XVIII') then being formed,
  one of the $G_1$ and $G_2$ represents a furane and the other one $G_1$ or $G_2$ represents a maleimide, a surfactant of formula (I) wherein G comprises a group G' representing a group of formula (XVII) then being formed,
  one of the $G_1$ and $G_2$ represents an aldehyde and the other one $G_1$ or $G_2$ represents an amine, a surfactant of formula (I) wherein G comprises a group G' representing a group of formula (XXI) then being formed,
  one of the $G_1$ and $G_2$ represents a phosphate of formula —O—P(=O)(OH)$_2$ and the other one $G_1$ or $G_2$ represents a hydroxyl, a surfactant of formula (I) wherein G comprises a group G' representing a group of formula (XXII) then being formed,
  one of the $G_1$ and $G_2$ represents a good leaving group LG and the other one $G_1$ or $G_2$ represents a group of the following formula

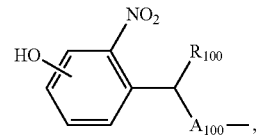

a surfactant of formula (I) wherein G comprises a group G' representing a group of formula (XXIV) wherein $A_{101}$ represents O then being formed,
  one of the $G_1$ and $G_2$ represents a hydroxyl or an amine —$NH_2$ and the other one $G_1$ or $G_2$ represents a group of the following formula

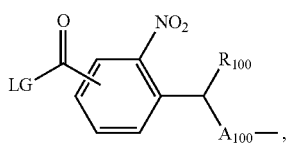

a surfactant of formula (I) wherein G comprises a group G' representing a group of formula (XXIV) wherein $A_{101}$ respectively represents —O—(CO)— or —NH—(CO) then being formed, one of the $G_1$ and $G_2$ represents a good leaving group LG and the other one $G_1$ or $G_2$ represents a hydroxyl, a surfactant of formula (I) wherein G comprises a group G' representing a group of formula (XXV) then being formed, one of the $G_1$ and $G_2$ represents a good leaving group LG and the other one $G_1$ or $G_2$ represents an amine —$NH_2$, a surfactant of formula (I) wherein G comprises a group G' representing a group of formula (XXVI) then being formed, one of the $G_1$ and $G_2$ represents an oxyamine —O—$NH_2$ and the other one $G_1$ or $G_2$ represents an aldehyde, a surfactant of formula (I) wherein G comprises a group G' representing a group of formula (XXVII) then being formed.

When the group G comprises several groups G', the selection of the groups reacting together: $G'_1$ and $G_1$ on the one hand and $G'_2$ and $G_2$ on the other hand, may be made in the same way, by replacing the groups $G_1$ or $G_2$ in the examples mentioned above with $G'_1$ or $G'_2$.

The compound of formula (LII) may either be an antigen as such when the latter comprises in the natural condition a group -$G_2$ which may be grafted to the surfactant of formula (LI), or a chemically modified antigen for grafting the desired group $G_2$ thereon (via the binding group $Z_1$), this chemical modification being carried out under conditions known to one skilled in the art.

The method may therefore comprise, before the contacting of the premix emulsion and of the compound of formula (LII) in order to form the surfactant bearing an antigen of formula (I), a step for preparing the compound of formula (LII) by chemically modifying an antigen for grafting the group $G_2$ thereon.

In an embodiment, the compound of formula (LII) is an antigen naturally bearing an amine function —$NH_2$. Mention may notably be made of protein antigens comprising at least one lysine.

For example, in order to prepare an immunogenic composition for which the surfactant of formula (I) has the formula (I') recalled below:

the method typically comprises:
the preparation of the compound of formula (LII') by chemical modification of an antigen bearing an amine function —$NH_2$ by reaction with (sulfosuccinimidyl-4-N-maleimidomethyl)cyclohexane-1-carboxylate) (sulfo-SMCC) according to the following reaction scheme:

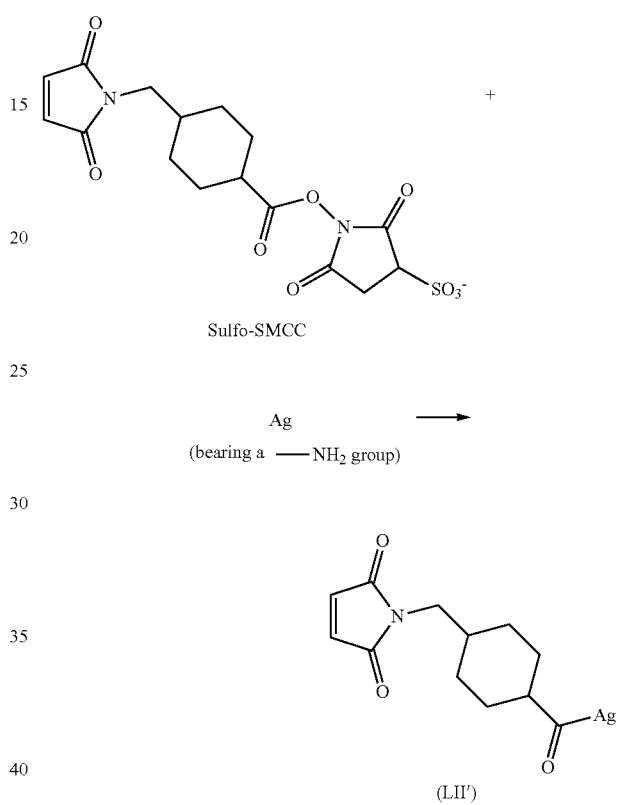

and then contacting, preferably carried out at a temperature from 0° C. to 15° C., notably from 0 to 10° C., preferably from 0 to 5° C.:
of a premix emulsion comprising a continuous aqueous phase and a phase dispersed as droplets, comprising an amphiphilic lipid, a solubilizing lipid comprising at least one fatty acid glyceride, a co-surfactant comprising at least one chain consisting of alkylene oxide units and a surfactant of the following formula (LI'):

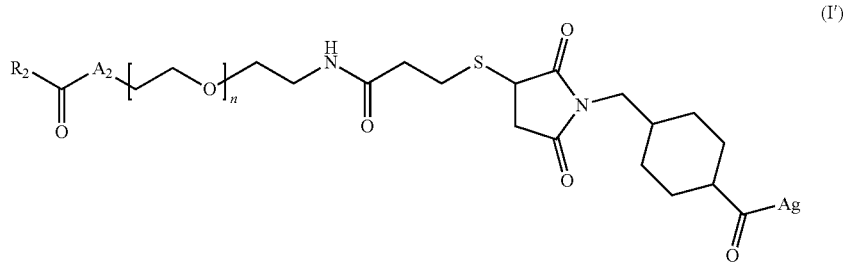

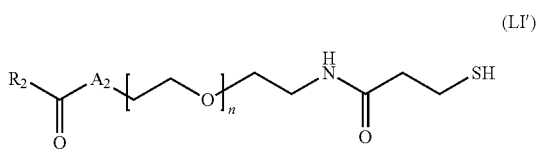

(LI')

wherein the molar ratio of the surfactant of formula (LI) over sum of the co-surfactant and of the surfactant of formula (LI') is from 0.01% to 5%, with the compound of formula (LII'), wherein $R_2$, $A_2$, n and Ag are as defined above.

Generally, the yield of the reaction between the surfactant of formula (LI) and the compound of formula (LII) (i.e. of the reaction for grafting the antigen onto droplets of the emulsion) is above 40%, notably above 50%, typically above 60%. Yields of more than 90% may be observed in certain embodiments. These yields are variable according to the applied chemical reaction (and therefore to the nature of the groups $G_1$ and $G_2$ or $G'_1$ and $G'_2$), according to the nature of the surfactant of formula (LI) (for example, beyond 200 ethylene oxide units in the group $H_1$, the poly(ethylene oxide) chain of the surfactant is folded over itself and the groups $G_1$ are less accessible for reacting with the compound of formula (LII)) and according to the nature of the antigen Ag (depending on its size, its charge, accessibility of function $Z_1$-$G_2$ in space . . . ).

The components of the immunogenic composition described above are commercially available and may be prepared by following procedures described in the literature.

Formation of the Premix Emulsion

The premix emulsion may easily be prepared by dispersing suitable amounts of oily phase and of aqueous phase under the effect of shearing, typically by a method including the steps:

(i) preparing an oily phase comprising an amphiphilic lipid and a solubilizing lipid comprising at least one fatty acid glyceride;

(ii) preparing an aqueous phase comprising a co-surfactant comprising at least one chain consisting of alkylene oxide units and a surfactant of formula (LI);

(iii) dispersing the oily phase in the aqueous phase under the action of sufficient shearing in order to form an emulsion; and (iv) recovering the thereby formed emulsion.

In this method, the different oily constituents are first mixed in order to prepare an oily premix for the dispersed phase of the emulsion. The mixing of the different oily constituents may optionally be facilitated by putting into solution one of the constituents or the complete mixture in a suitable organic solvent and by subsequent evaporation of the solvent, in order to obtain a homogenous oily premix for the dispersed phase. The selection of the organic solvent depends on the solubility of the constituents. The solvents used may for example be methanol, ethanol, chloroform, dichloromethane, hexane, cyclohexane, DMSO, DMF or further toluene. When this is an immunogenic composition intended to be administered, these are preferably volatile organic solvents and/or non-toxic for humans. Moreover, it is preferred to produce the premix at a temperature at which the whole of the ingredients is liquid.

Advantageously, the oily phase is dispersed in the aqueous phase in the liquid state. If one of the phases solidifies at room temperature, it is preferable to produce the mixture with one or preferably both phases heated to a temperature greater than or equal to the melting temperature, both phases being heated to a temperature preferably less than 80° C., and still preferentially less than 70° C., and further preferentially less than 60° C.

The emulsification under the effect of shearing is preferably achieved by means of a sonicator or a microfluidizer. Preferably, the aqueous phase and then the oily phase are introduced in the desired proportions in a suitable cylindrical container and the sonicator is then immersed in the medium and started for a sufficient period of time in order to obtain an emulsion, most often a few minutes.

The premix emulsion is generally a nanoemulsion. By the aforementioned method, a homogenous nanoemulsion is obtained, wherein the average diameter of the droplets is greater than 20 nm and less than 200 nm, notably from 50 to 120 nm.

Preferably, the zeta potential of the obtained emulsion is less than 25 mV in absolute value, i.e. comprised between −25 mV and 25 mV.

Before preparing the immunogenic composition according to the invention, the premix emulsion may be diluted and/or sterilized, for example by filtration or dialysis. This step gives the possibility of removing the possible aggregates which might be formed during the preparation of the emulsion.

The thereby obtained premix emulsion is ready for use, if necessary after dilution.

In the premix emulsion, the molar ratio of the surfactant of formula (LI) over the sum of the co-surfactant and of the surfactant of formula (LI) is from 0.01% to 5%. Indeed, it was shown that the grafting of the compound of formula (LII) on the droplets of the premix emulsion (by reaction with the surfactant of formula (LI)) is not efficient for molar ratios (surfactant of formula (LI))/(co-surfactant+surfactant of formula (LI)) greater than 5%.

[Uses of the Immunogenic Composition]

A Method for Producing Antibodies

The invention also relates to a method for producing monoclonal or polyclonal antibodies applying the immunogenic composition as defined above.

Thus, the invention relates to a method for producing polyclonal antibodies, comprising the steps consisting in:

(a) the immunization of an animal with an immunogenic composition as defined in any of claims 1 to 7, so as to induce a humoral immune response against said antigen, and (b) harvesting the induced polyclonal antibodies directed against said antigen.

The invention also relates to a method for producing monoclonal antibodies, comprising the steps consisting in:

(i) the immunization of an animal with an immunogenic composition according to the invention, (ii) recovering and isolating B lymphocytes of the immunized animal in step (i), (iii) producing a hybridoma and cultivating said hybridoma in order to produce monoclonal antibodies directed against the antigen present in said immunogenic composition, (iv) harvesting and purifying the monoclonal antibodies produced in step (iii).

The immunization in steps (a) and (i) is achieved by injecting the immunogenic composition according to the invention into an animal in an effective dose in order to induce a humoral immune response to an antigen as defined above. One skilled in the art is capable of determining the conditions required for immunization of the animals. Several immunization procedures are thus possible depending on the antigen present in the immunogenic composition according to the invention, for example by varying the doses, the intervals between injections, the duration of the treatment.

The animal used in the methods for producing antibodies according to the invention is an animal conventionally used for producing antibodies, i.e. a rodent (mouse, rat, hamster), a rabbit, a goat, a sheep, a monkey, a hen, a guinea pig, or a horse.

Optionally, in the methods for producing antibodies according to the invention, a control step, in the blood of the immunized animal, for the presence of antibodies directed against the antigen present in the immunogenic composition according to the invention is carried out after the immunization steps (a) or (i). This control step is carried out with conventional techniques known to one skilled in the art, for example by titration of the amount of antibodies in the serum of the immunized animal by ELISA.

In the method for producing polyclonal antibodies according to the invention, the step (b) for harvesting the induced polyclonal antibodies directed against said antigen is carried out with conventional techniques known to one skilled in the art. This step notably comprises a collection of the blood of the immunized animal (with or without sacrificing the animal), followed by isolation of the serum which contains the polyclonal antibodies, and optionally purification of the polyclonal antibodies.

In the method for producing monoclonal antibodies according to the invention, the recovery and isolation of the B lymphocytes in step (iii) is achieved with conventional techniques known to one skilled in the art. This step notably involves the sacrifice of the immunized animal, followed by removal of the spleen, and isolation of the B lymphocytes from the removed spleen.

The production of a hybridoma in step (iv) is achieved according to conventional techniques known to one skilled in the art, and notably involves the fusion of the B lymphocytes isolated in step (iii) with a myeloma, so as to produce a hybridoma. The fusion is for example achieved by using polyethylene glycol or by electroporation. The thereby obtained hybridoma is then cultivated under suitable conditions which may easily be determined by one skilled in the art so as to allow the hybridoma to secrete antibodies. Depending on the desired antibody production scale, this step for cultivating the hybridoma may notably be carried out in a bio-reactor.

In a last step (v), the thereby secreted antibodies are harvested and purified by means of conventional techniques known to one skilled in the art, such as for example high performance liquid chromatography, by affinity chromatography by using the G protein, or further by precipitation with ammonium.

Use as a Drug

The object of the invention is also an immunogenic composition as defined above for its use as a drug.

The invention also relates to an immunogenic composition as defined above for its use in order to induce an immune response against the antigen present in the immunogenic composition. Preferably, the immunogenic composition as defined above is used for inducing an immune response against the antigen present in the immunogenic composition in an individual to which said immunogenic composition is administered.

In certain embodiments, said immune response is a humoral immune response against the antigen present in the immunogenic composition.

In certain embodiments, the immunogenic composition according to the invention is used for treating or preventing an infection, cancer, an inflammatory disease or an allergy, depending on the nature of the antigen present in the immunogenic composition.

By "infection", is meant an infection caused by any pathogen, i.e. a virus, a bacterium, a yeast or a parasite. Preferably, the infection is an infection due to a pathogen from which at least one antigen as defined above is derived.

By "allergy", is meant an allergy due to any allergen. Preferably, the allergy is an allergy due to an allergen from which at least one antigen as defined above is derived.

By "inflammatory disease", is meant here a disease associated with inflammation. Examples of inflammatory diseases are well known to one skilled in the art and in particular include atherosclerosis, myocardial ischaemia, acne, asthma, auto-immune diseases, prostatitis, glomerulonephritis, hypersensitivities, intestinal chronic inflammatory diseases, pelvic inflammatory diseases, rheumatoid arthritis, graft rejection, vasculitis, interstitial cystitis, allergies and inflammatory myopathies.

By "cancer", is meant any cancer. Preferably, the cancer is a cancer from which at least one tumoral antigen as defined above is derived.

The immunogenic composition may be a composition with a prophylactic target or a therapeutic target, or both. Preferably, said immunogenic composition according to the invention is a vaccine.

In certain embodiments, said composition is administered to a human, including a man, a woman or a child, or to a non-human mammal, including a primate (monkey), a feline (cat), a canine (dog), a bovine (cow), an ovine (sheep, goat), an equine (horse), a porcine (pig), a rodent (rat, mouse, hamster, guinea pig), or a rabbit.

Immunization Method

The invention also relates to an immunization method against a disease in an individual requiring it comprising the administration to the individual of an immunogenic composition or of a vaccine according to the invention. Preferably, said immunogenic composition or said vaccine is administered in an immuno-protective dose.

By "individual requiring it", is meant an individual who develops or who risks developing a disease. The individual may be a human, including a man, a woman or a child, or a non-human mammal, including a primate (monkey), a feline (cat), a canine (dog), a bovine (cow), an ovine (sheep, goat), an equine (horse), a porcine (pig), a rodent (rat, mouse, hamster, guinea pig), or a rabbit.

In certain embodiments, the disease is an infection, an allergy, an inflammatory disease or a cancer. Preferably, said infection is a viral, bacterial, parasitic infection caused by a pathogen from which the antigen as defined above is derived. Preferably, said allergy is an allergy due to an allergen as defined above. Preferably, said cancer is a cancer from which the antigen as defined above is derived.

The administration method may be any administration method used in the field of vaccines. The immunogenic composition may notably be administered via an intradermal, intramuscular, topical, trans-cutaneous, cutaneous, mucosal, intranasal route. Preferably, when the immunogenic composition according to the invention is in gel form, it is administered via a cutaneous or mucosal route.

By "immuno-protective dose", is meant an amount capable of inducing a specific humoral and/or cell immune response. The humoral immune response is evaluated by detecting the presence of neutralizing antibodies in the serum of the vaccinated host according to techniques known to one skilled in the art. The cell immune response is evaluated by the detection of the presence of T lymphocytes CD4+, CD8+, and/or NK cells in the serum of the vaccinated host according to techniques known to one skilled in the art. The amount of composition or vaccine according to the present invention as well as the administration frequency will be determined by clinical studies, by the physician or by the pharmacist. The "immuno-protective dose" specific to each of the individuals may depend on a certain number of factors such as the nature and the severity of the disorder to be treated, the composition used, the age, the weight, the general health condition, the gender and the diet of the individual, the administration method, the duration of the treatment (in monodoses or in several doses), the drugs used in combination and other factors well known to medical specialists.

The administration volume may vary according to the administration method. Preferably, during administration via a sub-cutaneous route, the volume may be comprised between 0.1 ml and 10 ml.

The optimum moment for administering the immunogenic composition according to the invention is from about 1 week to 6 months, preferably from 1 month to 3 months, before the first exposure to the pathogen. The immunogenic composition may be administered as a prophylactic agent in hosts with the risk of developing a disease as defined above.

The immunogenic composition according to the invention may be administered in a single dose, or optionally the administration may involve the use of a first dose followed by a second dose ("booster" dose) which for example is administered 2 to 6 months later, as suitably determined by one skilled in the art.

The invention is illustrated upon considering the figures and examples which follow.

FIGURES

Figure 6:
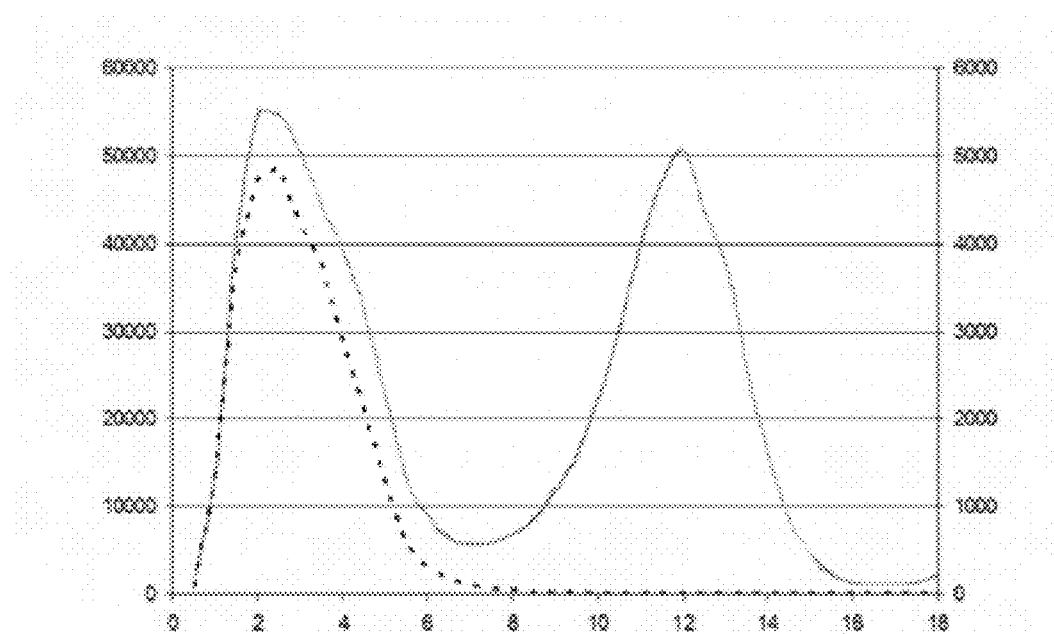

FIG. 6 provides the fluorescence intensity (ordinates) versus the elution volume in mL (abscissas) for ovalbumin (solid line) or for droplets (dotted line) (example 1 paragraph 1.2.2.).

Figure 7:
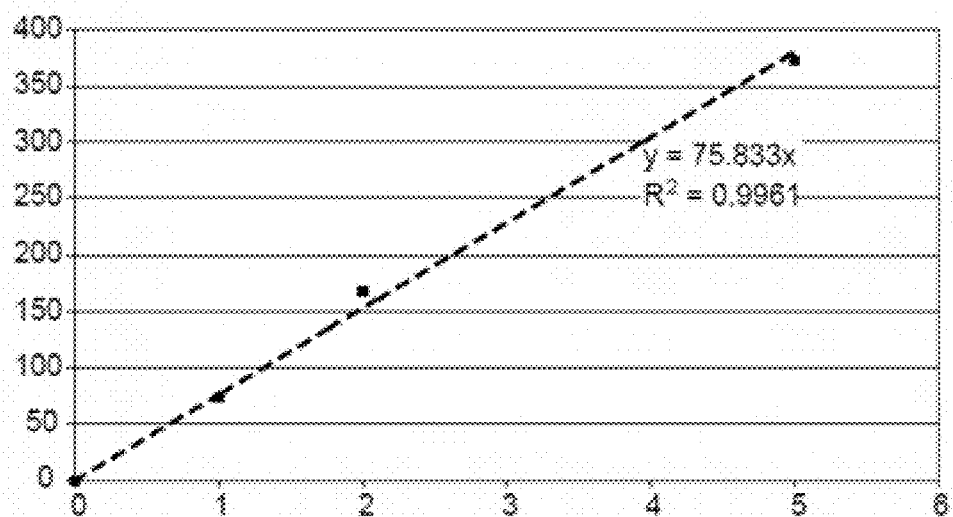

FIG. 7 provides the average ovalbumin number grafted per droplet (ordinates) versus the mass in mg of surfactant precursor of formula (LI') in the emulsion (abscissas), the squares corresponding to the experimental points and the dotted line to the linear extrapolation (example 1 paragraph 1.2.2.).

Figure 8:
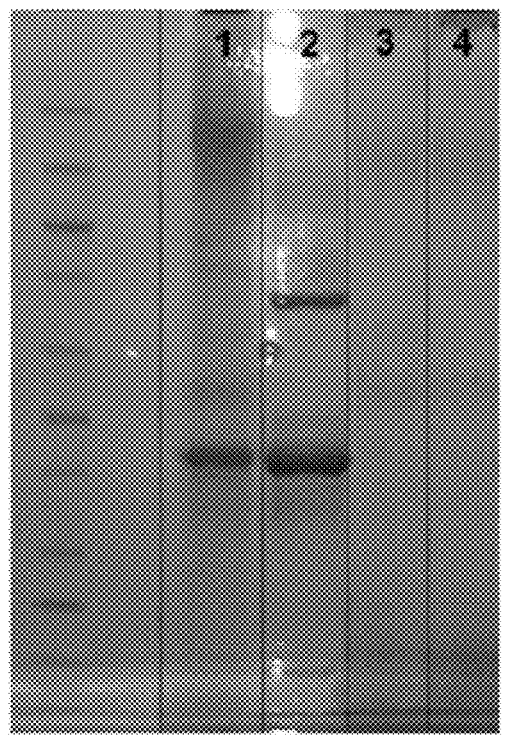

FIG. 8 is a photograph of an SDS-PAGE gel of 1) of ovalbumin functionalized by the surfactant of formula (LI'); 2) free of ovalbumin; 3) functionalized droplets by ovalbumin and from a premix emulsion B; 4) functionalized droplets by ovalbumin and from a premix emulsion B' (example 1 paragraph 1.2.2.).

Figure 9:
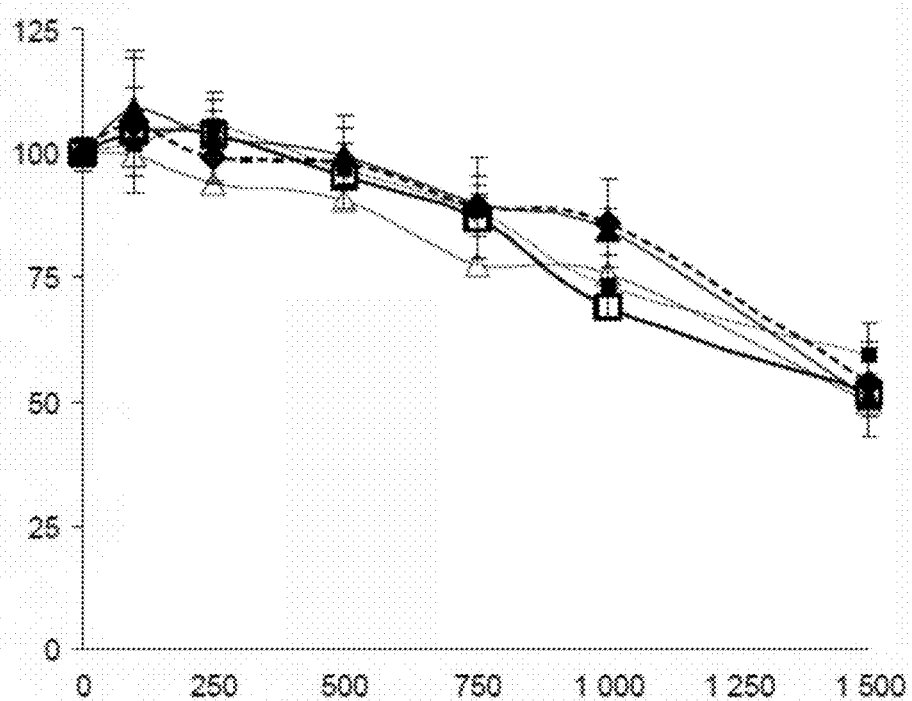

FIG. 9 provides the viability of a line of 3T3 fibroblasts in % (ordinates) versus the proportion in µg/mL of emulsion (abscissas) (Example 1 paragraph 1.2.5.).

Curve with solid diamonds, dotted line: fibroblasts incubated in the presence of droplets having 0% molar of functionalizable surfactant.

Curve of solid squares, solid line: fibroblasts incubated in the presence of droplets having 0.35% molar of functionalizable surfactant and for which the thiol functions have been "deactivated" by reaction with a maleimide —OH.

Curve of empty squares, solid line: fibroblasts incubated in the presence of droplets having 0.88% molar of functionalizable surfactant and for which the thiol functions have been deactivated by reaction with a maleimide —OH.

Curve with solid triangles, solid line: fibroblasts incubated in the presence of droplets having 0.35% molar of functionalizable surfactant on which the ovalbumin has been grafted.

Curve of empty triangles, solid line: fibroblasts incubated in the presence of droplets having 0.88% molar of functionalizable surfactant on which the ovalbumin has been grafted.

Figure 10:
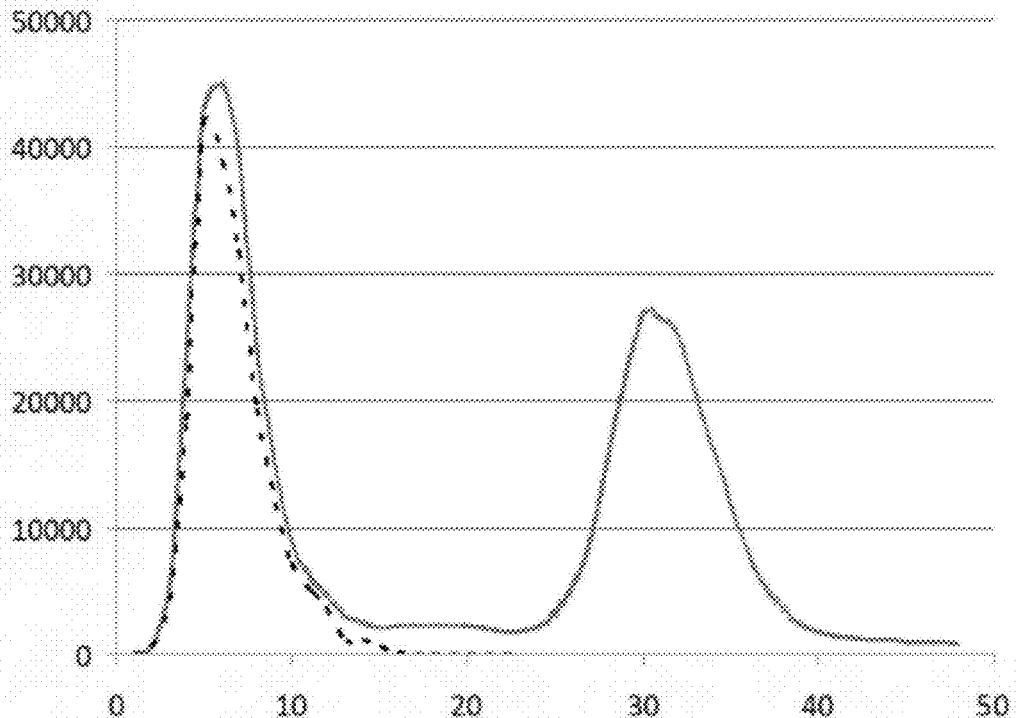

FIG. 10 provides the fluorescence intensity (ordinates) versus the elution volume in mL (abscissas) for the peptide (solid line) or for the droplets (dotted line) (Example 2).

Figure 11:
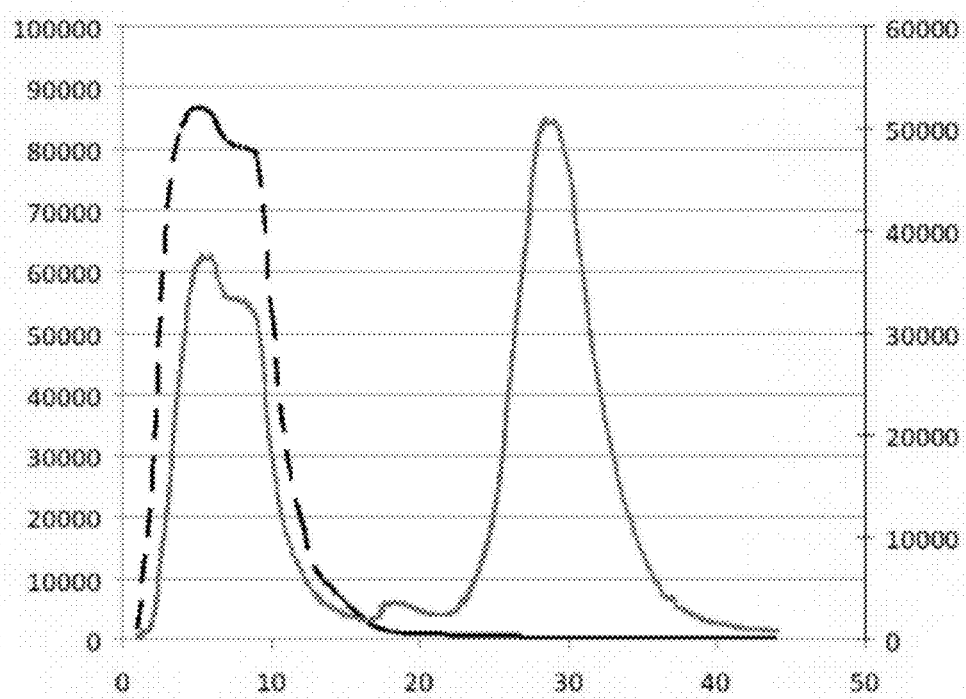

FIG. 11 provides the fluorescence intensity (ordinates) versus the elution volume in mL (abscissas) for the peptide (solid line) or for the droplets (dotted line) (Example 3).

Figure 12:
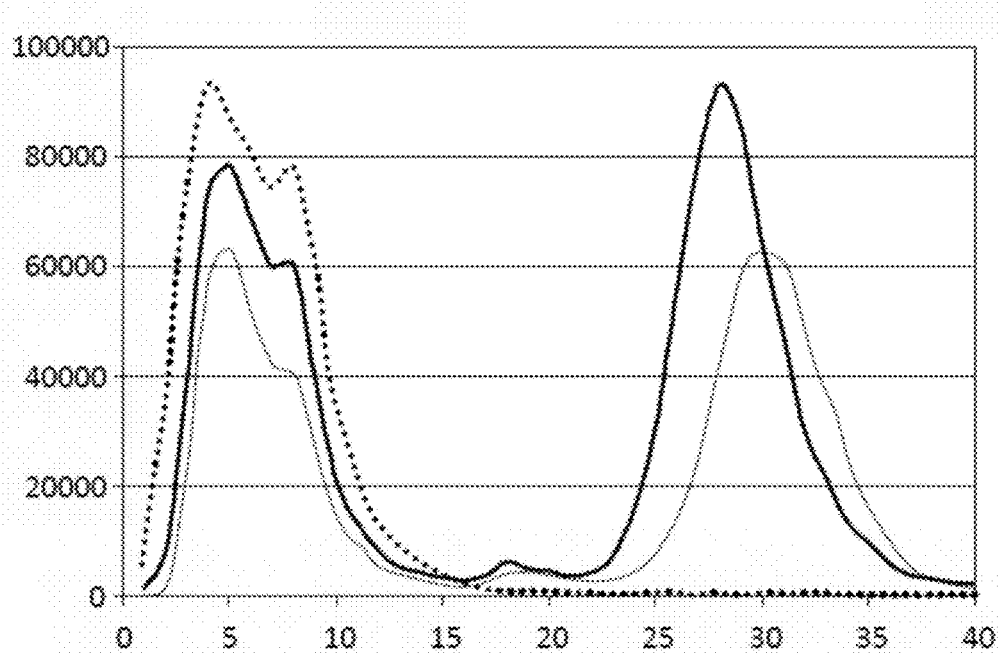

FIG. 12 provides the fluorescence intensity (ordinates) versus the elution volume in mL (abscissas) for the peptide (solid line) or for droplets (dotted line) (Example 4).

Figure 13:
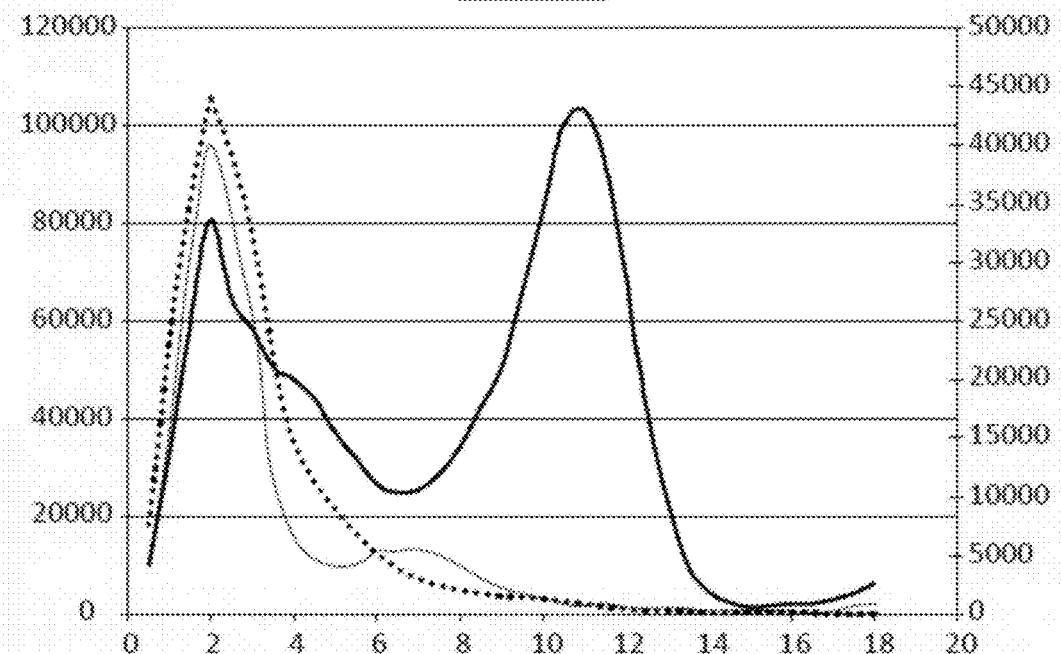

FIG. 13 illustrates the fluorescence intensity (ordinates) versus the volume in mL (abscissas) for ovalbumin (thick solid line), the antibodies (thin solid line) and the droplets (dotted line) (Example 7).

Figure 14:
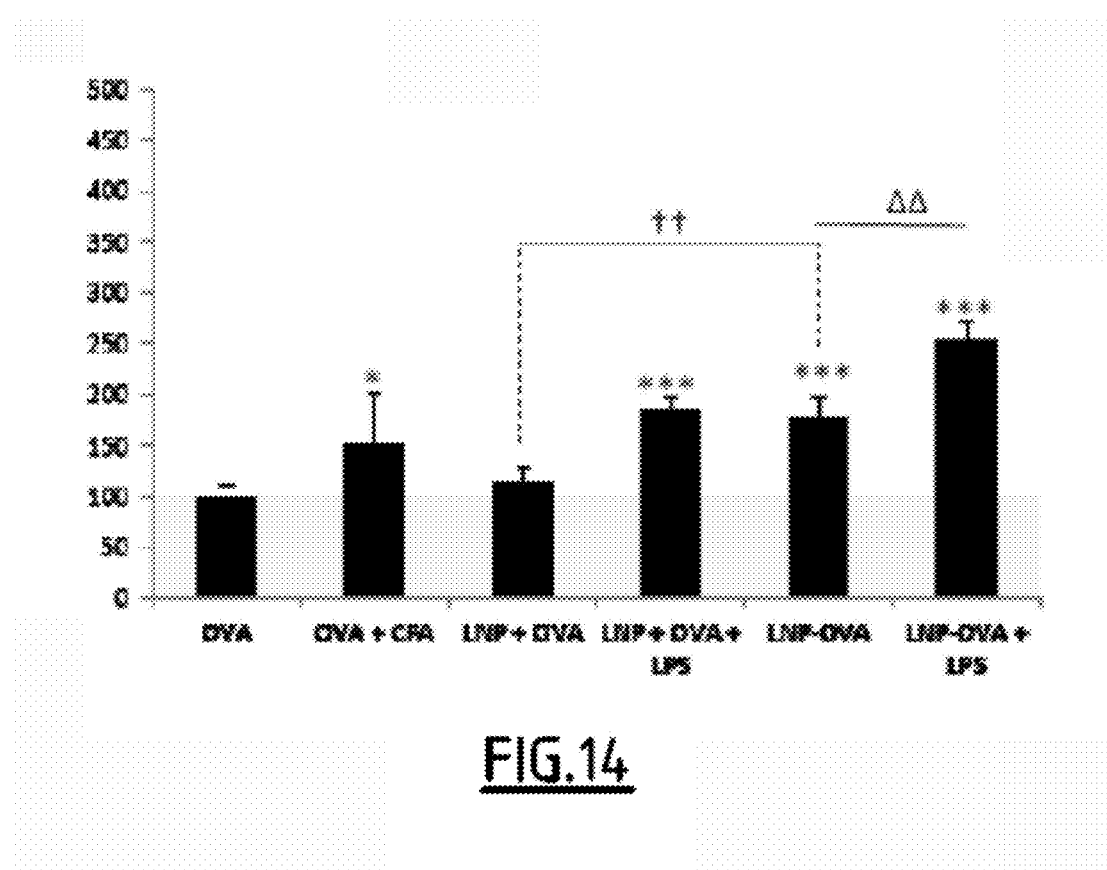

FIG. 14 illustrates the immunization results obtained for n=4 individuals, i.e. the percentage of anti-ovalbumin antibody (% OVA) (ordinates) depending on the composition used:

OVA for administration of ovalbumin alone without any vector (comparative),

OVA+CFA for administration of ovalbumin alone without any vector and of CFA adjuvant (comparative), LNP+OVA for administration of ovalbumin and of emulsion droplets, the ovalbumin not being bound to the droplets (comparative), LNP+OVA+LPS for the administration of ovalbumin, of emulsion droplets and of an immunostimulating agent LPS, the ovalbumin not being bound to the droplets and the LPS not being incorporated into the droplets (comparative), LNP-OVA for the administration of ovalbumin covalently bound to the emulsion droplets (immunogenic composition according to the invention), LNP-OVA+LPS for the administration of ovalbumin covalently bound to the emulsion droplets, and LPS not being incorporated into the droplets.

\* $p<0.05$; \*\*\* $p<0.001$ compared with the OVA controls; †† $p<0.01$; ΔΔ $p<0.01$ (Example 8).

Figure 15:
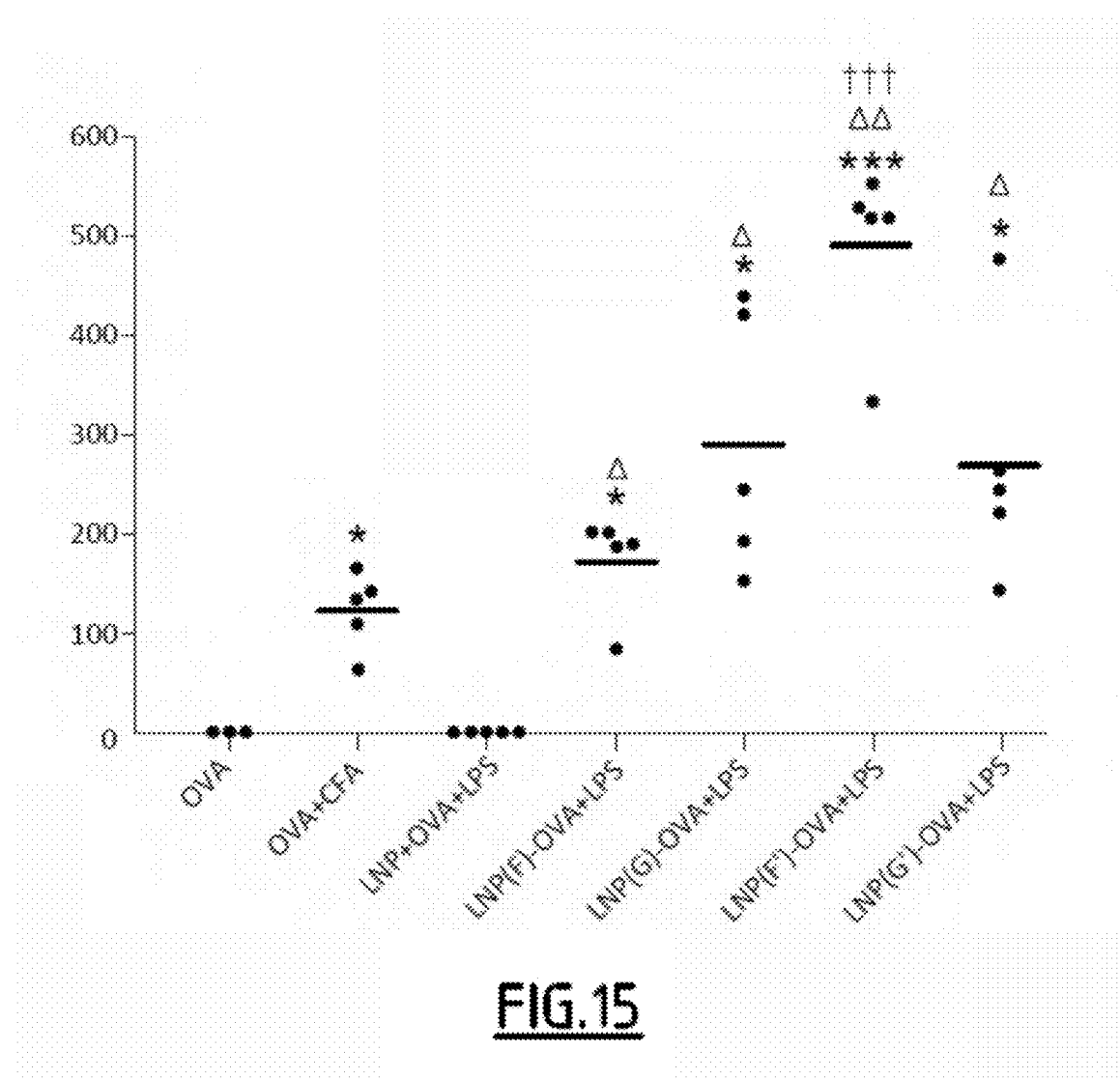

FIG. 15 illustrates the immunization results obtained for n=5 individuals, i.e. the proportion of total anti-OVA Ig (ng/mL) in the sera of mice immunized by ovalbumin (ordinates) depending on the used composition:

OVA for the administration of ovalbumin alone without any vector (comparative),

OVA+CFA for the administration of ovalbumin alone without any vector and of CFA adjuvant (comparative), LNP+OVA+LPS for the administration of ovalbumin, emulsion droplets F at Example 1.1.2 and of an immunostimulating agent LPS, the ovalbumin not being bound to the droplets of the emulsion and the LPS not being incorporated into the droplets of the emulsion (comparative), LNP(F)-OVA+LPS for the administration of emulsion droplets F grafted with ovalbumin obtained in Example 1.2.2 (immunogenic composition according to the invention) and of the immunostimulating agent LPS, the LPS not being incorporated into the droplets, LNP(G)-OVA+LPS for the administration of emulsion droplets G grafted with the ovalbumin obtained in Example 1.2.2 (immunogenic composition according to the invention) and of immunostimulating agent LPS, the LPS not being incorporated into the droplets, LNP(F')-OVA+LPS for the administration of emulsion droplets F' grafted with ovalbumin obtained in Example 1.2.2 (immunogenic composition according to the invention) and of immunostimulating agent LPS, the LPS not being incorporated into the droplets, LNP(G')-OVA+LPS for the administration of emulsion droplets G' grafted with ovalbumin obtained in Example 1.2.2 (immunogenic composition according to the invention) and of immunostimulating agent LPS, the LPS not being incorporated into the droplets.

Wilcoxon test: *
* $p<0.05$; *** $p<0.001$ as compared with OVA
Δ $p<0.05$; ΔΔ, $p<0.01$ as compared with OVA+CFA
††† $p<0.001$ as compared with LNP(F)-OVA+LPS (Example 8).

EXAMPLES

Example 1: Preparation of an Immunogenic Composition Comprising a Surfactant Bearing an Antigen (Ovalbumin) of Formula (I')

1.1. Preparation of the Premix Emulsion

A premix emulsion comprising a surfactant of formula (LI') wherein $R_2$ represents $C_{17}H_{35}$, $A_2$ represents NH and n represents 100, i.e. of the following formula:

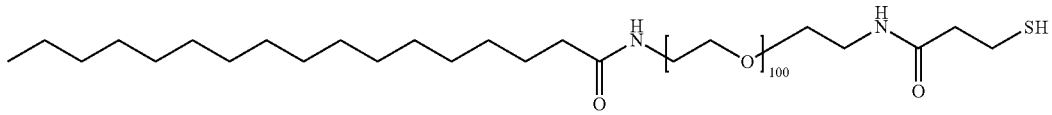

was prepared as follows.

1.1.1. Preparation of a Precursor of the Surfactant of Formula (LI')

A precursor of the surfactant of formula (LI') wherein the end thiol function is protected by an —S-pyridinyl group was prepared by following the following reaction scheme:

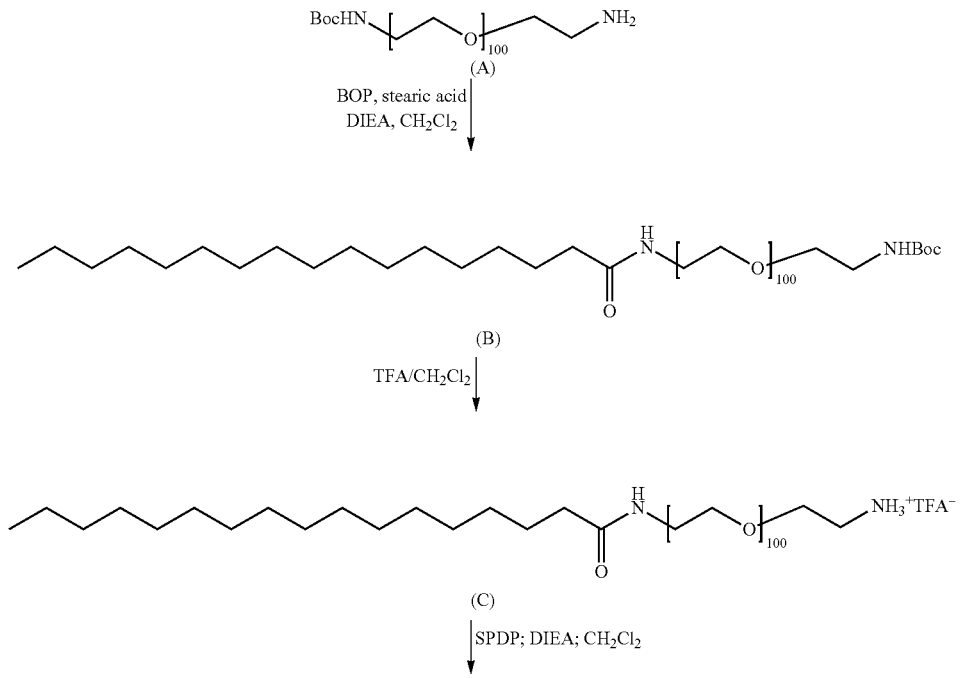

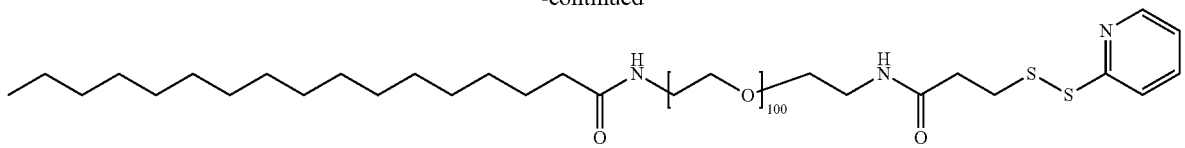

Synthesis of the Compound (B)

Stearic acid (2 g; 0.6 mmol) and benzotriazole-1-yl-oxy-tris-(dimethylamino)-phosphonium hexafluorophosphate (BOP) (265.2 mg; 0.6 mmol) were dissolved in $CH_2Cl_2$ (15 ml). After 10 minutes of stirring, BocNH-PEG100-$NH_2$ (MW: 4,928; 2 g; 0.4 mmol) (compound (A)) and diisopropylethylamine (DIEA) (104.5 ml; 0.6 mmol) were added to the reaction medium. The disappearance of the initial amine was checked by thin layer chromatography (TLC) ($CH_2Cl_2$/MeOH). After 2 hours with stirring, the product precipitated from cold ether, was dissolved in a minimum of water and then dialyzed against milli Q water (cut-off: 1,000). The solution was then recovered and the water was removed either by evaporation (ethanol as an azeotrope) or by freeze-drying, in order to obtain 1.5 g of a compound (B) (white powder), i.e. a yield of 70%.

TLC ($CH_2Cl_2$/MeOH 9/1): Rf=0.5

$^1$H NMR (300 MHz; CDCl3): d: 0.87 (t; J=6.5 Hz; 3H; C$\underline{H_3}$—$CH_2$); 1.24 (m; 28H; 14C$\underline{H_2}$); 1.44 (s; 9H; C(C$\underline{H_3}$)$_3$); 1.67 (quin; 2H; C$\underline{H_2}$—$CH_2$—CONH); 2.42 (t; J=7.5 Hz; 2H; C$\underline{H_2}$—CONH); 3.3 (t; J=5.0 Hz; 2H; BocNH—C$\underline{H_2}$); 3.45-3.8 (m; 362H; xC$\underline{H_2}$(PEG), $CH_2$CONH—C$\underline{H_2}$)

Synthesis of Compound (C)

The compound (B) (1.5 g; 0.29 mmol) was dissolved in 10 ml of dichloromethane and 4 ml of trifluoroacetic acid (TFA). The conversion into compound (C) was tracked by TLC (ninhydrin as a developer). After 1 hour with stirring, the solvent was evaporated by coevaporation with toluene (which removes the TFA). The product was dried in vacuo in order to obtain 1.3 g of compound (C) (white powder), i.e. a yield of 86.7%

TLC ($CH_2Cl_2$/MeOH 9/1): Rf=0.27

$^1$H NMR (300 MHz; CDCl$_3$): d: 0.87 (t; J=6.5 Hz; 3H; C$\underline{H_3}$—$CH_2$); 1.24 (m; 28H; 14C$\underline{H_2}$); 1.60 (quin; 2H; C$\underline{H_2}$—$CH_2$—CONH); 2.15 (t; J=7.5 Hz; 2H; C$\underline{H_2}$—CONH); 3.17 (bt; 2H; C$\underline{H_2}$—$NH_3^+$); 3.4 (m; 2H; $CH_2$CONH—C$\underline{H_2}$); 3.5-3.8 (m; 360H; xC$\underline{H_2}$(PEG)); 6.14 (bs; 1H; N$\underline{H}$CO); 7.9 (bs; 2H; N$\underline{H_2}$/N$\underline{H_3}$+)

Synthesis of the Precursor of the Surfactant of Formula (LI')

Under argon, some compound (C) (0.5 g; 0.1 mmol) and DIEA (52 ml; 0.3 mmol) were dissolved in dichloromethane (10 ml). After 5 minutes with stirring with succinimidyl 3-(2-pyridyldithio)propionate (SPDP) (93 mg; 0.3 mmol) were added into the reaction medium. The disappearance of the amine was followed by TLC ($CH_2Cl_2$/MeOH 9/1). After 1 hour of reaction, the product precipitated twice from ether so as to obtain after filtration 400 mg of precursor (yellowish powder) i.e. a yield of 76%

TLC ($CH_2Cl_2$/MeOH 9/1): Rf=0.42

$^1$H NMR (300 MHz; CDCl3): d: 0.88 (t; J=6.5 Hz; 3H; C$\underline{H_3}$—$CH_2$); 1.25 (m; 28H; 14C$\underline{H_2}$); 1.63 (quin; 2H; C$\underline{H_2}$—$CH_2$—CONH); 2.17 (t; J=7.5 Hz; 2H; C$\underline{H_2}$—CONH); 2.62 (t; J=7 Hz; 2H; C$\underline{H_2}$—SS); 3.09 (t; J=7 Hz; 2H; NHCO—C$\underline{H_2}$—$CH_2$—SS); 3.42 (m; 2H; C$\underline{H_2}$—NHCO); 3.48-3.8 (m; 360H; xC$\underline{H_2}$(PEG); C$\underline{H_2}$—NHCO); 6.11 (bt; 1H; NH); 6.79 (bt; 1H; NH); 7.11 (m; 1H; CHpyr); 7.67 (m; 2H; 2CHpyr); 8.49 (m; 1H; CHpyr)

1.1.2. Preparation of Premix Emulsions Comprising the Surfactant of Formula (LI')

The premix emulsion was prepared by following the procedures described in WO 2010/018223 with the compositions indicated in Tables 2 and 3, complete dissolution of Myrj S40 and of the surfactant of formula (LII) in the aqueous phase having required the heating of the solution to 60° C. The aqueous and oily phases are then mixed and then emulsified by sonication according to the parameters described in Table 4.

TABLE 2

Formulation of the premix emulsions of diameter 120 nm comprising the precursor of the surfactant of formula (LI')

| | Amphiphilic lipid lecithin S75 (Lipoïd) (mg) | Solubilizing lipid Suppocire ® NB (Gattefossé) (mg) | Cationic lipid (DOTAP) (mg) | Soya oil (Croda) (mg) | PBS 1X (µL) | cosurfactant MYRJ S40 (CRODA) (PEG 40) mg | mmol | precursor mg | mmol | Precursor/(precursor + co-surfactant) ratio (%) mol % | mass % |
|---|---|---|---|---|---|---|---|---|---|---|---|
| A | 45 | 450 | 0 | 150 | 1140 | 214 | 107 | 1 | 0.19 | 0.18 | 0.47 |
| B | 45 | 450 | 0 | 150 | 1140 | 213 | 106.5 | 2 | 0.37 | 0.35 | 0.94 |
| C | 45 | 450 | 0 | 150 | 1140 | 210 | 105 | 5 | 0.94 | 0.88 | 2.33 |
| D | 45 | 450 | 0 | 150 | 1140 | 205 | 102.5 | 10 | 1.87 | 1.79 | 4.65 |
| E | 45 | 450 | 0 | 150 | 1140 | 195 | 97.5 | 20 | 3.75 | 3.70 | 9.30 |
| F | 45 | 450 | 0 | 150 | 1140 | 210 | 105 | 5 | 0.94 | 0.88 | 2.33 |
| G | 11 | 450 | 34 | 150 | 1140 | 210 | 105 | 5 | 0.94 | 0.88 | 2.33 |

In Table 2, « precursor » means precursor of the surfactant of formula (LI'), « % mol » means molar % and « mass % » means % by mass.
In the 7 premix emulsions, the total mass of (precursor of the surfactant of formula (LI') + co-surfactant) is always 215 mg.

TABLE 3

Formulation of the premix emulsions of diameter 80 nm comprising the precursor of the surfactant of formula (LI').

|  | Amphiphilic lipid lecithin S75 (Lipoïd) (mg) | Solubilizing lipid Suppocire ® NB (Gattefossé) (mg) | Cationic lipid (DOTAP) (mg) | Soya oil (Croda) (mg) | PBS 1X (µL) | cosurfactant MYRJ S40 (CRODA) (PEG 40) mg | cosurfactant MYRJ S40 (CRODA) (PEG 40) mmol | precursor mg | precursor mmol | Precursor/ (precursor + cosurfactant) ratio (%) mol % | Precursor/ (precursor + cosurfactant) ratio (%) mass % |
|---|---|---|---|---|---|---|---|---|---|---|---|
| A' | 50 | 307.5 | 0 | 102.5 | 1240 | 299 | 149.5 | 1 | 0.19 | 0.13 | 0.33 |
| B' | 50 | 307.5 | 0 | 102.5 | 1240 | 298 | 149 | 2 | 0.37 | 0.25 | 0.67 |
| C' | 50 | 307.5 | 0 | 102.5 | 1240 | 295 | 147.5 | 5 | 0.94 | 0.63 | 1.67 |
| D' | 50 | 307.5 | 0 | 102.5 | 1240 | 290 | 145 | 10 | 1.87 | 1.28 | 3.33 |
| E' | 50 | 307.5 | 0 | 102.5 | 1240 | 280 | 140 | 20 | 3.75 | 2.61 | 6.67 |
| F' | 50 | 307.5 | 0 | 102.5 | 1240 | 295 | 147.5 | 5 | 0.94 | 0.63 | 1.67 |
| G' | 12 | 307.5 | 38 | 102.5 | 1240 | 295 | 147.5 | 5 | 0.94 | 0.63 | 1.67 |

In Table 3, « precursor » means precursor of the surfactant of formula (LI'), « mol % » means molar % and « mass % » means % by mass.
In the 7 premix emulsions, the total mass of (precursor of the surfactant of formula (LI') + cosurfactant) is 300 mg.

The increase in the amount of precursor of the surfactant of formula (LI') in the emulsions could only be achieved for (surfactant of formula (LI')+co-surfactant)/(precursor of the surfactant of formula (LI')+co-surfactant) molar ratios of less than 5%. Beyond these molar ratios, the emulsions are not stable and the droplets aggregate and form a highly viscous medium which cannot be used for grafting the antigen.

TABLE 4

Sonication parameters used with a sonicator AV505 ® (Sonics, Newtown, USA)

| Probe (φ) | Power Pmax | Sonication time | Pulse on/off |
|---|---|---|---|
| 3 mm | 28% | 20 min | 10 s/30 s |

The thereby produced premix emulsions comprise droplets comprising a precursor of the surfactant of formula (LI') for which the thiol function is protected by the —S-pyridinyl group which have been de-protected so as to be able to covalently graft the antibody onto the droplets.

Figure 1:
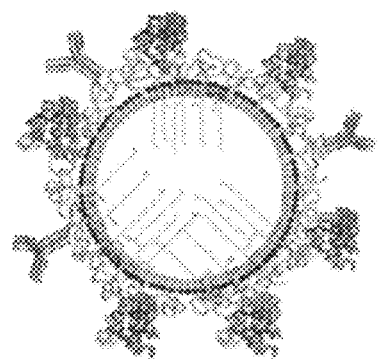
FIG. 1 illustrates a diagram illustrating a section of an immunogenic composition droplet according to the invention. On the crown are illustrated antigens covalently grafted to the droplets (by surfactants of formula (I)), targeting agents (mannosylated lipid or antibody) and immunostimulating agents.
Figure 2:
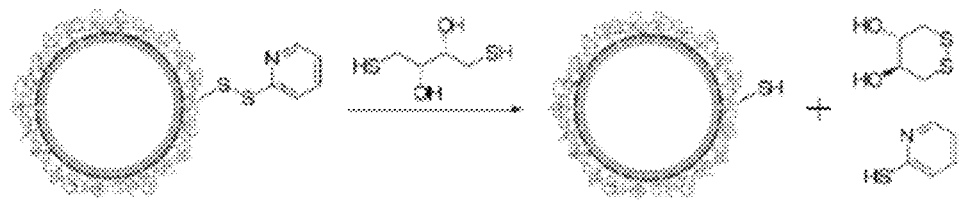
FIG. 2 illustrates the reaction scheme for de-protecting the precursor of the surfactant of formula (LI') by cleaving the group —S-pyridinyl in order to release the thiol function which will subsequently be used for grafting the ovalbumin antigen (example 1 paragraph 1.1.2.).
Figure 3:
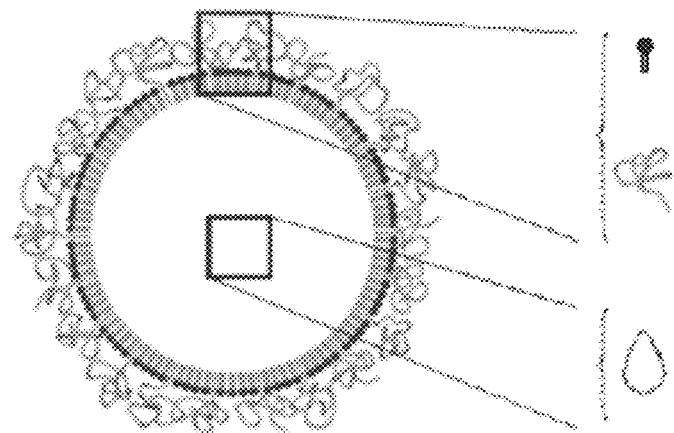
FIG. 3 illustrates a diagram illustrating a section of a premix emulsion droplet of example 1 paragraph 1.1.2. The core of the droplets comprises the oil and the solubilizing lipid, and the crown comprises the amphiphilic lipid, the co-surfactant and the surfactant of formula (LI').

In order to do this, the premix emulsions were incubated with 4 mg of dithiothreitol for 1 hour with magnetic stirring at room temperature. The premix emulsions were then purified by dialysis (cut-off threshold: 12 kDa, versus PBS 1×, four times for 1 h and then one night) for removing the components which are not integrated to the droplets as well as the secondary products from the de-protection, as illustrated in FIG. 2. A section of a droplet of a premix emulsion is schematized in FIG. 3.

In order to check that the surfactants of formula (LI') were actually incorporated into the droplets and bearers of free thiol functions, a fluorophore-maleimide (Fluoprobe 647-H maleimide from Interchim) was grafted on these thiol functions in order to assay them. The results, provided in Table 5, showed more than 95% of the surfactants of formula (LI') were incorporated into the droplets in their —SH form.

TABLE 5

Dosage of the —SH functions on the droplets.

| Premix emulsions | A | B | C | D | A' | B' | C' | D' |
|---|---|---|---|---|---|---|---|---|
| Amount of precursor of surfactant of formula (LI') initially introduced into the formulation (mg) | 1 | 2 | 5 | 10 | 2.5 | 5 | 7.5 | 10 |
| % of precursor of the surfactant of formula (LI') actually incorporated into the droplets | 96.8 | 96.3 | 97.4 | 98.4 | 40.2 | 40.1 | 59.7 | 71.5 |
| Theoretical average number of —SH functions per droplets for 100% incorporation | 125 | 250 | 625 | 1260 | 104 | 209 | 313 | 418 |
| Actual average number of —SH functions per droplets considering actual incorporation | 121 | 241 | 609 | 1238 | 42 | 84 | 187 | 299 |
| Average size (nm) after deprotection | 116.6 ± 2.4 | 118.4 ± 1.8 | 115.1 ± 2.7 | 112.2 ± 2.5 | 78.9 ± 0.7 | 75.9 ± 4.9 | 77.5 ± 0.5 | 74.1 ± 5.2 |

Further, the sizes of the droplets of the 8 premix emulsions A, B, C, D, A', B', C' and D' of Table 5 were measured by DLS (instrument Zetasizer Nano ZS from Malvern Instruments, UK). The droplets of the 4 premix emulsions A, B, C and D have a diameter of the order of 120 nm. The droplets of the 4 premix emulsions A', B', C' and D' have a diameter of the order of 80 nm.

1.2. Grafting of Ovalbumin on the Droplets of the Premix Emulsions Prepared According to 1.1.

1.2.1. Preparation of the Compound of Formula (LII') by Chemical Modification of Ovalbumin in Order to Graft Thereon the Group $G_2$ of the Maleimide Type The ovalbumin was selected as a model antigen to be grafted on the droplets since it is known that it has two epitopes of different classes known for producing a cell response (MHC-I) and a humoral response (MHC-II):

OVA 257-264: SIINFEKL (SEQ ID No. 1),
OVA 323-339: ISQAVHAAHAEINEAGR (SEQ ID No. 2).

This is a globular protein of 45 kDa with an isoelectric pH of 4.5. It has 6 cysteine functions for which none are chemically accessible without prior denaturation of the protein and 20 lysine functions, for which only 3 are chemically accessible without prior denaturation of the protein (Steven et al., *Biochem J.*, 1958, 70, 179-182).

In order to graft ovalbumin on the thiol functions present at the surface of the droplets of the premix emulsions prepared according to paragraph 1.1, it was necessary to introduce one or several maleimide functions on the protein, via a bifunctional linker: sulfosuccinimidyl 4-(N-maleimidomethyl)cyclohexane-1-carboxylate (sulfo-SMCC) according to the following reaction scheme. For this, the ovalbumin in solution was reacted in PBS 1× with 10 to 50 equivalents of sulfo-SMCC with magnetic stirring for 1 h at room temperature.

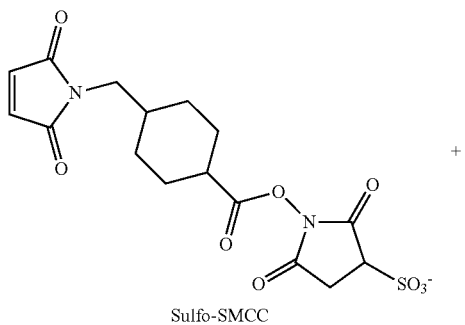

Sulfo-SMCC

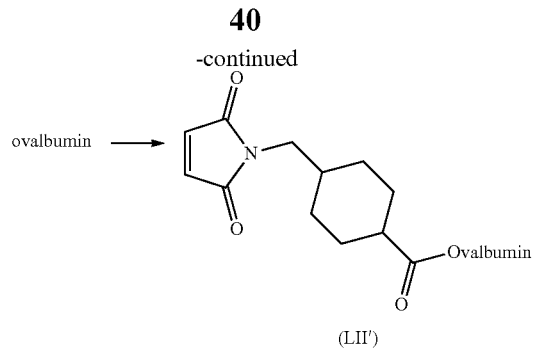

(LII')

In order to be able to subsequently quantify the yield of the chemical modification reaction of ovalbumin, a sample was taken and the ovalbumin was marked with a fluorophore of the NHS-ester or isothiocyanate type, for example FITC, by adding the latter to the reaction medium for further one hour.

The protein was then separated from the excess of reagents by steric exclusion chromatography on a PD-10 column.

Figure 4:
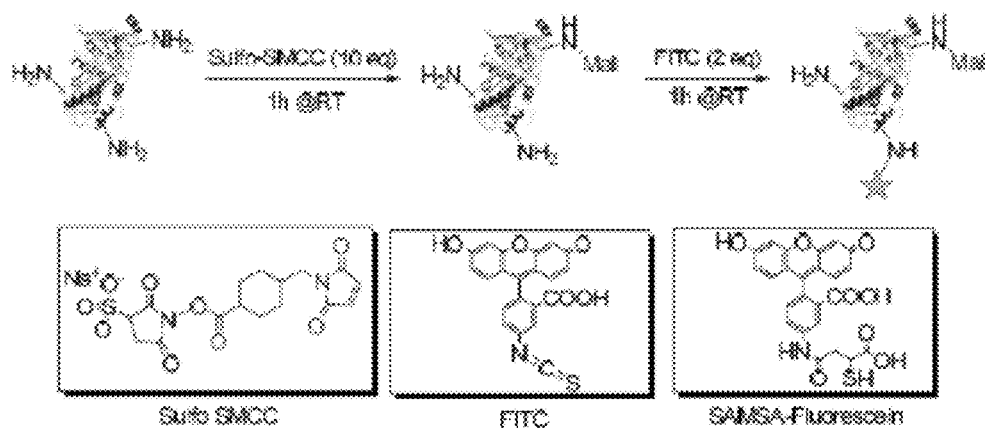
FIG. 4 illustrates the reaction scheme for chemically modifying of ovalbumin for grafting thereon a maleimide group (being subsequently used for grafting the modified ovalbumin to the droplets of the emulsion) and a fluorophore (example 1 paragraph 1.2.1.).

In order to quantify the number of reactive maleimide functions introduced onto the protein, the latter were assayed in fluorescence by reaction with a fluorophore bearing a thiol function such as SAMSA-Fluorescein as illustrated in FIG. 4.

This fluorescence assay gave the following results for 10 and 50 equivalents of sulfo-SMCC:

10 equiv.: 0.73 maleimide per ovalbumin (i.e. a functionalization yield of 24%)
50 equiv.: 1.23 maleimide per ovalbumin (i.e. a functionalization yield of 41%)

These conditions therefore seem ideal in order to obtain an average of one maleimide per ovalbumin and therefore to avoid the formation of covalent bonds between the droplets: droplet-ovalbumin-droplet during grafting.

1.2.2. Grafting Method—Reaction Between the Surfactant of Formula (LI') Bearing a Group $G_1$ of the —SH Type and the Compound of Formula (LII') Bearing a Group $G_2$ of the Maleimide Type.

The compound of formula (LII') (ovalbumin functionalized by a maleimide) was purified, in solution in PBS 1×, and was placed with magnetic stirring at 0-4° C. in an ice water bath. The premix emulsion was then slowly added dropwise with a (compound of formula (LII')/(thiol contained in the premix emulsion of 1.1/1) ratio. The grafting occurred by forming the surfactant of the following formula (I):

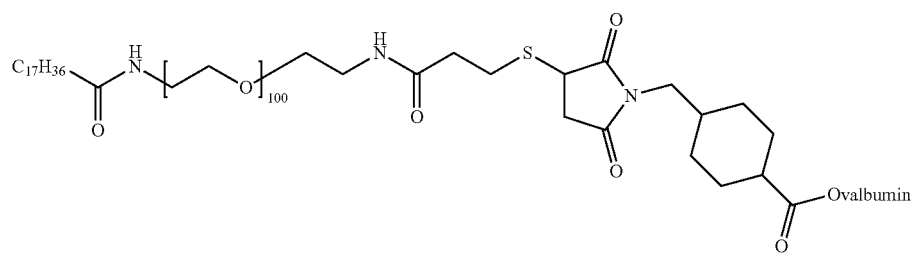

Figure 5:
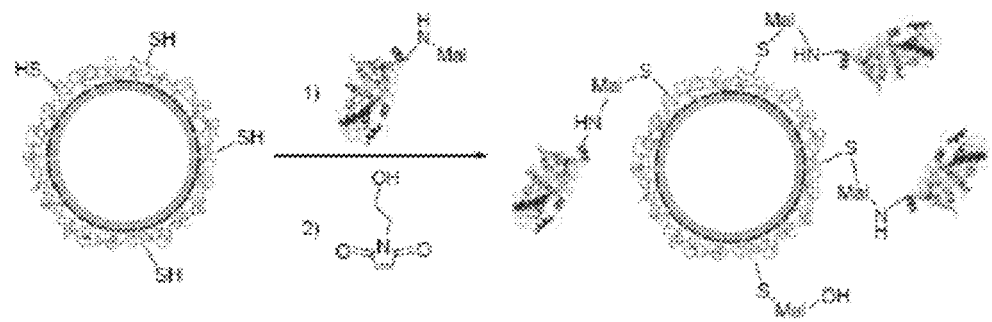
FIG. 5 illustrates the reaction scheme for grafting modified ovalbumin on a premix droplet and then for blocking the remaining thiol functions with Mal-OH (example 1 paragraph 1.2.2.).

Stirring was maintained for several hours until the temperature again rises to 20° C. and then 1-(2-hydroxyethyl)-1H-pyrrole-2,5-dione (Mal-OH) was added with a Mal-OH/thiol ratio of 3/1 so as to consume the unreacted thiol functions, as illustrated in FIG. 5.

The obtained emulsions were then purified by steric exclusion chromatography on a Superdex 200 resin by harvesting 500 μL fractions after passage of the dead volume of the column. The elution profiles of the droplets loaded with fluorophores and of the labeled protein were tracked in fluorescence. An exemplary result of fluorescence is given in FIG. 6.

The fluorescence signal of the grafted ovalbumin is correlated with the fluorescence signal of the droplets. The grafted ovalbumin/free ovalbumin percentage was obtained by evaluating the ratio between the areas under the curve for grafted ovalbumin and non-grafted ovalbumin. The number of moles of grafted ovalbumin, the functionalization yield and the average number of ovalbumin per droplet were then calculated. For a same premix emulsion, the relationship between the average number of ovalbumin per droplet and the amount of available thiols is linear, as shown by the example of emulsion B indicated in FIG. 7.

By considering that ovalbumin is a globular protein with a diameter of 6 nm (according to Malvern), it was possible to calculate the surface percentage of a droplet covered with grafted ovalbumin. A maximum surface coverage of 23% was obtained.

The droplets bearing ovalbumin were analyzed in SDS-PAGE after purification by steric exclusion chromatography. No line specific to ovalbumin appears in the purified droplets, which shows the efficiency of the separation by steric exclusion chromatography (FIG. 8).

1.2.3. Physicochemical Characterization of the Obtained Emulsions

The hydrodynamic diameter and the surface potential of the droplets on which the ovalbumin was grafted were determined by DLS/ELS (Zetasizer Nano ZS instrument from Malvern Instruments, UK).

An increase in the hydrodynamic diameter was observed after grafting of ovalbumin (Table 6). This increase depends on the number of grafted ovalbumin on the droplets and seems to attain a plateau.

TABLE 6

Physical properties of the droplets before and after grafting of ovalbumin.

| Premix emulsion used | A | B | C | B' |
|---|---|---|---|---|
| Amount of precursor of surfactant of formula (LI') initially introduced into the premix emulsion (mg) | 1 | 2 | 5 | 1 |
| Average number of ovalbumin per droplet | 74 | 168 | 373 | 59 |
| Hydrodynamic diameter before grafting (nm) | 113.0 ± 0.6 | 115.0 ± 2.1 | 112.4 ± 2.3 | 81.2 ± 2.1 |
| Hydrodynamic diameter after grafting (nm) | 133.4 ± 3.3 | 139.3 ± 5.3 | 161.2 ± 5.2 | 106.2 ± 2.6 |
| PdI before grafting | 0.104 ± 0.016 | 0.087 ± 0.007 | 0.099 ± 0.003 | 0.170 ± 0.005 |
| PdI after grafting | 0.107 ± 0.002 | 0.103 ± 0.012 | 0.192 ± 0.016 | 0.233 ± 0.005 |

| Premix emulsion used | F | G | F' | G' |
|---|---|---|---|---|
| Amount of precursor of surfactant of formula (LI') initially introduced into the premix emulsion (mg) | 5 | 5 | 5 | 5 |
| Average number of ovalbumin per droplet | 373 | 373 | 60 | 60 |
| Hydrodynamic diameter before grafting (nm) | 119 ± 1 | 123 ± 3 | 81 ± 2 | 82 ± 3 |
| Hydrodynamic diameter after grafting (nm) | 157 ± 2 | 160 ± 4 | 98 ± 3 | 103 ± 2 |
| PdI before grafting | 0.129 ± 0.014 | 0.114 ± 0.015 | 0.170 ± 0.005 | 0.146 ± 0.010 |
| PdI after grafting | 0.196 ± 0.013 | 0.198 ± 0.017 | 0.208 ± 0.011 | 0.187 ± 0.006 |
| Zeta potential (Zp) before grafting | −6 ± 1 | +6 ± 1 | −7 ± 3 | +6 ± 1 |
| Zeta potential (Zp) after grafting | −8 ± 1 | +4 ± 1 | −8 ± 1 | +4 ± 1 |

In spite of the increase in size observed after grafting of ovalbumin, the hydrodynamic diameter remained in a range of interesting size for applications in vaccination, i.e. a droplet size of less than 200 nm for promoting cellular internalization.

As regards the surface potential of the droplets, it remained the same before and after grafting, i.e. comprised between −7 and −10 mV (measured in PBS 0.1×).

1.2.4. Colloidal Stability of the Obtained Emulsions

The stability of the droplets on which ovalbumin was grafted having the highest ovalbumin load level (emulsion C grafted with ovalbumin obtained in 1.2.2.) was checked by observing the time-dependent change in the hydrodynamic diameter, of the surface potential PdI and of the zeta potential of the droplets placed at 4° C. for 150 days. No change in these parameters over time was observed, which demonstrates the stability of the emulsions.

1.2.5. Toxicity of the Droplets on which Ovalbumin was Grafted

Droplets on which ovalbumin was grafted (emulsion A grafted with ovalbumin and emulsion C grafted with ovalbumin obtained in 1.2.2. FIG. 9 curves with the triangles) were subject to a toxicity test in order to check their impact on the line of 3T3 fibroblasts. Emulsions without any surfactant of formula (I) or (LI') (without any ovalbumin, FIG. 9 curves with squares, and without any functionalizable surfactant, FIG. 9 curve with dotted line, diamonds) were used as a control. The concentration of droplets (in µg/ml) is indicated in abscissas and the cell viability (in % of living cells) is indicated in ordinates. The IC50 determined by this method was the same for all the droplets on which the ovalbumin was grafted and identical with that of the control emulsions. This shows that the grafting at the surface of ovalbumin does not at all affect the good tolerance of the fibroblasts 3T3 to the latter.

Example 2: Preparation of an Immunogenic Composition Comprising a Surfactant Bearing an Antigen (Peptide) of Formula (I')

The peptide which was used in these experiments is the epitope with cell response (MHC-I) of ovalbumin, i.e. the sequence OVA 257-264: S-I-I-N-F-E-K-L (8-mer) SEQ ID NO:1. This peptide was modified so as to graft a fluorophore thereon: 6-carboxy-fluorescein (Fam™), by adding a lysine at the C-terminal end, and a maleimide function (Mal) on the N-terminal end by the sub-contractor Smartox Biotechnology. The obtained peptide therefore has the following sequence: Mal-S-I-I-N-F-E-K-L-K-6-carboxy-fluorescein (SEQ ID NO:3).

This peptide was reacted with a premix emulsion B as prepared in Example 1 (see 1.1.2.) but further encapsulating an agent of interest: a fluorophore, DiD. The purification of a reaction mixture by steric exclusion chromatography on a gel then exhibited a fluorescence signal of the peptide (FIG. 10, solid line) correlated with a fluorescence signal of the droplets (FIG. 10, dotted line). According to the results of FIG. 10, it is estimated that each droplet bears on average 181 peptides (coupling yield of 60%).

Example 3: Preparation of an Immunogenic Composition Comprising a Surfactant Bearing an Antigen (Peptide) of Formula (I')

The peptide which was used in these experiments is the epitope with humoral response (MHC-II) of ovalbumin, i.e. the sequence OVA 323-339: I-S-Q-A-V-H-A-A-H-A-E-I-N-E-A-G-R (17-mer) (SEQ ID NO:2). The peptide Ova 323-339 was modified so as to graft thereon a fluorophore: carboxytetramethylrhodamine (Tamra™) on the N-terminal end and a maleimide function (Mal) on the C-terminal end by the sub-contractor Smartox Biotechnology. The obtained peptide therefore has the following sequence: Mal-I-S-Q-A-V-H-A-A-H-A-E-I-N-E-A-G-R-carboxytetramethylrhodamine (SEQ ID NO:4). This peptide was reacted with a premix emulsion B as prepared in Example 1 (see 1.1.2.) but encapsulating a fluorophore, DiD. The purification of the reaction mixture by steric exclusion chromatography on a gel then exhibited a fluorescence signal of the peptide (FIG. 11, solid line) correlated with a fluorescence signal of the droplets (FIG. 11, dotted line). According to the results of FIG. 11, it is estimated that each droplet on average bears 99 peptides (coupling yield of 40%).

Example 4: Preparation of an Immunogenic Composition Comprising a Surfactant Bearing Two Antigens (Peptides) of Formula (I')

The peptides which were used in these experiments are the epitope with cell response (MHC-I) of ovalbumin, i.e. the sequence OVA 257-264 S-I-I-N-F-E-K-L (8-mer) (SEQ ID NO:1) and the epitope with humoral response (MHC-II) of ovalbumin, i.e. the sequence OVA 323-339 I-S-Q-A-V-H-A-A-H-A-E-I-N-E-A-G-R 17-mer) (SEQ ID NO:2). The peptide OVA 257-264 was modified so as to graft thereon a fluorophore: 6-carboxy-fluorescein (Fam™), by adding a lysine at the C-terminal end, and a maleimide function (Mal) on the N-terminal end by the sub-contractor Smartox Biotechnology. The obtained peptide therefore has the following sequence: Mal-S-I-I-N-F-E-K-L-K-6-carboxy-fluorescein (SEQ ID NO:3). The peptide Ova 323-339 was modified so as to graft thereon a fluorophore: carboxytetramethylrhodamine (Tamra™) at the N-terminal end and a maleimide function (Mal) at the C-terminal end by the sub-contractor Smartox Biotechnology. The obtained peptide therefore has the following sequence: Mal-I-S-Q-A-V-H-A-A-H-A-E-I-N-E-A-G-R-carboxytetramethylrhodamine (SEQ ID NO:4). These peptides then reacted with a premix emulsion B as prepared in Example 1 (see 1.1.2.) but encapsulating a fluorophore, DiD. The purification of the reaction mixture by steric exclusion chromatography on a gel then exhibited a fluorescence signal of the peptides (FIG. 12, two curves in solid lines) correlated with a fluorescence signal of the droplets (FIG. 12, dotted line). According to the results of FIG. 12, it is estimated that each droplet on average bears 76 peptides OVA 257-264 and 51 peptides OVA 323-339 (coupling yield of 43% for each of the peptides).

Example 5: Preparation of an Immunogenic Composition Comprising a Surfactant Bearing an Antigen of Formula (I') and an Immunostimulating Agent: MPLA The second installment consists, after having covalently grafted the ovalbumin antigen in the droplets, of incorporating into the droplets an immuno-adjuvant MPLA which will increase the immune response. This adjuvant was inserted into the crown of the droplets.

5.1. Encapsulation of MPLA in Premix Emulsions Comprising the Surfactant of Formula (LI')

MPLA (or lipid A) is an immunoadjuvant lipid, authorized since 2009 by the FDA for use in humans (Cervarix, Papillomavirus, GSK). It is one of the main constituents of the lipopolysaccharide (LPS) which itself partly forms the wall of bacteria.

Once it is purified, the lipid A always has an immunostimulating activity like LPS but with less toxicity, which makes it a first choice adjuvant. Because of its lipid nature, it is inserted very well at the surface of the hydrophobic nano-objects such as PLGA nanoparticles, or further liposomes, with encapsulation yields ranging from correct to very good yields. The MPLA is generally encapsulated at mass charge levels ranging from 0.1 to 1%, charge levels which are sufficient for obtaining a positive effect on the activation of the immune system.

In order to encapsulate MPLA into the droplets, the latter was dissolved in the molten oily phase before sonication. The MPLA was encapsulated at theoretical mass load levels from 0.1, 0.4 and 1.3% for which not very many modifications of the physicochemical properties were observed. The size of the droplets containing the MPLA only significantly increases for a theoretical mass load level of 1.3% (Table 7).

TABLE 7 physicochemical characterization of the droplets comprising encapsulated MPLA (so called «LNP(MPLA)») at different load levels.

| Theoretical DLE MPLA (% m/m) | Hydrodynamic diameter (nm) | PdI |
|---|---|---|
| 0 | 109.2 ± 0.8 | 0.104 ± 0.027 |
| 0.1 | 109.1 ± 0.4 | 0.096 ± 0.011 |
| 0.4 | 124.7 ± 4.8 | 0.154 ± 0.007 |
| 1.3 | 133.6 ± 1.1 | 0.181 ± 0.013 |

Consequently, the load level of 0.4% was retained subsequently. The dosage of MPLA by endotoxin dosages via the LAL (limulus amebocyte lysate) kit shows an incorporation yield of 95% i.e. a load level of 0.38%.

5.2. Grafting of Ovalbumin on Droplets of the Premix Emulsions Prepared According to 5.1.

Subsequently, droplets containing 0.4% (m/m) of MPLA and the precursor of the surfactant of formula (LI') (bearing the terminal group SPDP) (5 mg introduced into the formulation) were prepared, activated and purified as described in Example 1. The grafting and purification were carried out under the same conditions. The obtained emulsions have physicochemical properties identical with the emulsions prepared without any MPLA.

The grafting of ovalbumin on the droplets comprising encapsulated MPLA (so called «LNP(MPLA)» droplets) was carried out as described in Example 1 and the droplets comprising MPLA and ovalbumin (so-called «LNP-MPLAOva» droplets) which are obtained, have physicochemical properties close to those of LNP-Ova.

The grafting reaction led to an average number of ovalbumin per LNP(MPLA) of 413, close to the 373 obtained under the same conditions for LNPs without MPLA according to Example 1.

5.3. Colloidal Stability of the LNP(MPLA)-Ovas

The study of the stability at 4° C. of these LNP(MPLA)-Ovas did not show any particular modification at the physicochemical characteristics and confirms that the surface modification with ovalbumin as well as the insertion of the lipid A within the crown of droplets does not reduce their colloidal stability (Table 8).

TABLE 8

Stability of the LNP(MPLA)-Ovas preserved at 4° C.

| Time at 4° C. (days) | Hydrodynamic diameter (nm) | PdI |
|---|---|---|
| 0 | 148.6 ± 3.0 | 0.120 ± 0.011 |
| 50 | 151.1 ± 4.1 | 0.147 ± 0.005 |

Example 6: Targeting Immune Cells with a Composition Comprising a Biological Targeting Agent: Mannan (LNP-Mannan)

Mannan is a linear polymer of mannose. It is produced by *Saccharomyces Cerevisiae* and does not have any defined average molar mass.

The mannan was functionalized in the same way as of ovalbumin (see 1.2.1) and reacted with a premix emulsion B (see 1.1). The obtained droplets have a load level of mannan of 0.5% and were tested. For this load level, no significant modification of size or surface appeared. Macrophages were incubated with the LNP-Mannans containing a fluorophore (DiD) and then the fluorescence within the cells was measured by flow cytometry after one hour and three hours of incubation. The results show that the droplets bearing mannan are significantly more captured by the macrophages after one hour of incubation (FIG. 9, Table 9). Further, after 3 h of incubation, the average fluorescence intensity in the cells in contact with the LNP-Mannans is significantly greater, which shows that these cells have captured more droplets than the cells put into contact with the control droplets.

TABLE 9 cell capture results on the macrophages

| | Proportion of positive cells after 1 h of incubation | Proportion of positive cells after 3 h of incubation | Average fluorescence intensity per cell after 1 h of incubation | Average fluorescence intensity per cell after 3 h of incubation |
|---|---|---|---|---|
| Control | 0.3 ± 0.01% | 73.2 ± 0.7% | 1873 ± 225 | 1843 ± 25 |
| Mannan | 43.5 ± 0.6% | 85.2 ± 1.5% | 1442 ± 44 | 2593 ± 36 |

Example 7: Preparation of an Immunogenic Composition Comprising a Surfactant Bearing an Antigen (Ovalbumin) of Formula (I') and a Surfactant Bearing an Antibody of Formula (I')

One possibility for targeting the cells of the immune system was to produce covalent grafting of antibodies on the thiol functions of the surfactant of formula (LI') while maintaining the possibility of grafting the ovalbumin covalently to the droplets subsequently.

To do this, a model antibody functionalized by Sulfo-SMCC, Cetuximab and bearing a fluorophore A, Alexa700-NHS, was reacted with a premix emulsion as prepared in Example 1 but further encapsulating a fluorophore B, DiO, in a stoichiometric ratio Cetuximab/SH 1/10, such that only a low proportion of thiol functions will be occupied by the antibody. The reaction medium was then reacted without any preliminary purification, with the chemically modified ovalbumin in order to bear:
  a maleimide group allowing grafting to the thiol functions of the remaining surfactant of formula (LI') (chemical modification like in Example 1 (see 1.2.1.)) and
  a fluorophore C, Cy5-NHS.

The fluorophores A, B and C were selected so that it was not possible to have any energy transfer between them. The purification of the final reaction mixture by steric exclusion chromatography on a gel then showed the existence of bi-functionalized droplets bearing both an antibody and ovalbumin (fluorescence signal A, FIG. 13, curve in thin solid line) correlated with a fluorescence signal B, FIG. 13, curve in dotted line and with a fluorescence signal C, (FIG. 13, curve in thick solid line), as illustrated in FIG. 13. According to the results of FIG. 13, it is estimated that each droplet on average bears 44 antibodies (coupling yield of 80%) and 244 ovalbumins (coupling yield of 42%).

Example 8: Biological Use of the Immunogenic Composition According to Example 1. Immunization—Validation In Vivo of the Droplets on which Ovalbumin was Grafted Hereafter, the droplets on which ovalbumin was grafted, obtained in Example 1 are designated by « LNP-OVA ».

BALB mice of 8 weeks old received a first injection of LNP-Ova with or without LPS. The negative controls are obtained by injecting free ovalbumin with or without LPS as well as the free ovalbumin accompanied by «naked» LNP droplets (i.e. without any protein grafted at their surface) with or without LPS. After 21 days, a second booster injection is carried out and the mice are sacrificed on the 28$^{th}$ day. The anti-OVA antibody levels in the sera are then determined by ELISA.

Percentage of anti-ovalbumin antibodies (% OVA) versus the composition used (FIG. 14) The LNP droplets are those of the emulsion grafted with ovalbumin obtained in Example 1.2.2. The immunization with free ovalbumin without LPS gives a small immune response normalized to 100% (OVA, FIG. 14). The addition of a conventional veterinary adjuvant (CFA: complete Freund adjuvant) to the injection of ovalbumin gives a stronger immune response but with strong inter-individual heterogeneity (OVA+CFA, FIG. 14). A negative control was produced by injecting naked droplets with free ovalbumin, with or without adjuvant (LNP+OVA, LNP+OVA+LPS, FIG. 14). The observed responses are the same as those for OVA and OVA+CFA, which shows that the naked droplets are very well tolerated and do not activate the immune system. Finally, the injection of LNP-OVA leads to a significantly larger immune response than free ovalbumin (LNP-OVA vs. OVA, FIG. 14) and of the same order of magnitude as the responses obtained with free ovalbumin and adjuvants. This result shows that simple vectorization of ovalbumin by the droplets produces an effect similar to the addition of an adjuvant. As a reminder, LNP-OVAs do not contain any adjuvant. The addition of an adjuvant in addition to the LNP-OVA further and significantly increases the response (LNP-OVA+LPS, FIG. 14). As a conclusion, these immunization experiments validate the benefit of vectorization of the ovalbumin antigen by the emulsion according to the invention.

Proportion of total anti-OVA Ig (ng/ml) depending on the composition used (FIG. 15) For each composition, 50 μg of ovalbumin (either grafted or not to the emulsion droplets) were injected. The amount of injected ovalbumin is therefore the same for all the injected compositions.

The immunization with free ovalbumin without LPS gave a small immune response (OVA, FIG. 15).

The addition of an adjuvant conventionally used in the veterinary field (CFA: complete Freund adjuvant) to the injection of ovalbumin induced a larger immune response than that of the protein administered alone, characterized by a more significant level of anti-ovalbumin circulating antibodies (OVA+CFA, FIG. 15).

In every case, the injection of LNP-OVA (i.e. the emulsions according to the invention having ovalbumin grafted covalently at the surface) caused a significantly larger immune response than those induced by free ovalbumin or by ovalbumin in CFA (FIG. 15).

In particular, the highest level of anti-ovalbumin antibodies for a same administered dose of ovalbumin is observed following the injection of the emulsion F' grafted with ovalbumin obtained in Example 1.2.2, notably characterized by a lesser inter-individual response variability.

For the formulations of neutral droplets (emulsions F and F' grafted with ovalbumin obtained in Example 1.2.2, without any cationic lipid), the size seems to be a predominant criterion in the induced response level, insofar that the emulsion F grafted with ovalbumin obtained in Example 1.2.2 (diameter of 157 nm) significantly induced a response:

more significant than OVA+CFA and less significant than the one obtained with the emulsion F' grafted with ovalbumin as obtained in Example 1.2.2 (diameter of 98 nm).

On the other hand, the formulations of cationic droplets (emulsions G and G' grafted with ovalbumin obtained in Example 1.2.2, comprising the cationic lipid DOTAP), induce a humoral response of the same order, which is however more significant than the one obtained with OVA+CFA (FIG. 15). In this specific case, the size does not seem to be a determining factor.

These results show that vectorization of the ovalbumin by the droplets of the emulsions potentializes the immune responses. Indeed, it is important to observe that the induced immune responses are very small when the antigenic protein OVA is administered in a solution containing naked droplets (on which OVA is not covalently grafted) and LPS (LNP+OVA+LPS, FIG. 15), which emphasizes the significance of the existence of the covalent bond between ovalbumin and the droplets.

Further, the spleens of the mice were sampled when the mice were sacrificed, dissociated and the thereby harvested splenocytes were put back into culture and re-exposed to the ovalbumin protein. Next, the supernatants were collected and the cytokines were dosed by the CBA technique (CBA for cytometry beads assay).

The results showed that the emulsion F' grafted with ovalbumin obtained in Example 1.2.2 used in the immunization procedure is the one which induces the strongest secretion of cytokines IL-17, INFγ, IL10 and TNFα, as compared with the others from the emulsions F, G and G' grafted with ovalbumin obtained in Example 1.2.2 and with ovalbumin alone (OVA) or with ovalbumin in CFA (OVA+CFA) (Table 10).

It is interesting to note that the secretion of IFNγ is also more significant, as compared with ovalbumin in CFA (OVA+CFA) when the emulsion F grafted with ovalbumin obtained in Example 1.2.2 was used in the immunization procedure. Similarly, the TNFα level is higher when the emulsion G grafted with ovalbumin obtained in Example 1.2.2 was used in the immunization procedure.

TABLE 10

Proportions of cytokines IL-17, INFγ, IL10 and TNFα measured in mouse spleens.

| | OVA (comparative) | OVA + CFA (comparative) | OVA + LNP + LPS (comparative) | LNP (F)- OVA + LPS | LNP (F')- OVA + LPS | LNP (G)- OVA + LPS | LNP (G')- OVA + LPS |
|---|---|---|---|---|---|---|---|
| IL-10 (pg/ml) | 22 ± 21 | 31 ± 11 | 16 ± 7 | 27 ± 11 | 54 ± 26 | 34 ± 25 | 21 ± 13 |
| IL-17 (pg/ml) | 133 ± 31 | 217 ± 177 | 16 ± 8 | 275 ± 161 | 415 ± 209 | 196 ± 144 | 180 ± 69 |
| TNFα (pg/ml) | 73 ± 36 | 151 ± 54 | 150 ± 66 | 174 ± 38 | 315 ± 126 | 324 ± 148 | 161 ± 45 |
| IFN-γ (pg/ml) | 22 ± 34 | 19 ± 20 | 4 ± 5 | 79 ± 41 | 213 ± 120 | 41 ± 31 | 35 ± 28 |

The invention claimed is:

1. An immunogenic composition comprising a continuous aqueous phase and a dispersed phase as droplets and comprising:
   an amphiphilic lipid,
   a solubilizing lipid comprising at least one fatty acid glyceride,
   a co-surfactant comprising at least one chain consisting of alkylene oxide units,
   a surfactant bearing an antigen of the following formula (I'):

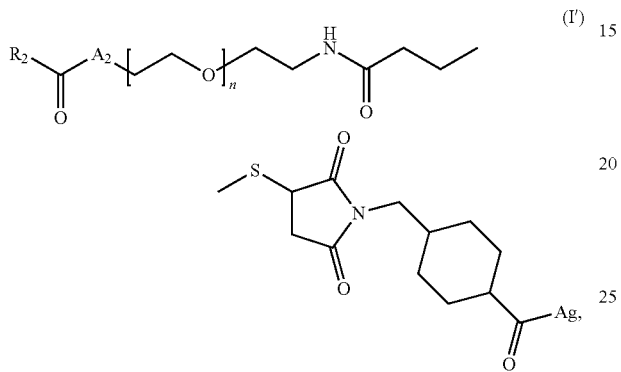

wherein:
   $R_2$ represents a linear hydrocarbon chain comprising from 7 to 23 carbon atoms,
   $A_2$ represents O or NH
   n represents an integer from 3 to 500, and
   Ag represents an antigen, and
wherein the molar ratio of the surfactant bearing an antigen of formula (I') over the sum of the co-surfactant and of the surfactant bearing an antigen of formula (I') is from 0.01% to 5%.

2. The immunogenic composition according to claim 1, wherein:
   the amphiphilic lipid is a phospholipid, and/or
   the solubilizing lipid consists of a mixture of saturated fatty acid glycerides including at least 10% by weight of $C_{12}$ fatty acids, at least 5% by weight of $C_{14}$ fatty acids, at least 5% by weight of $C_{16}$ fatty acids and at least 5% by weight of $C_{18}$ fatty acids, and/or
   the co-surfactant is selected from polyethyleneglycol/phosphatidyl-ethanolamine conjugate compounds, fatty acid and polyethyleneglycol ethers, fatty acid and polyethyleneglycol esters and block copolymers of ethylene oxide and propylene oxide, and the polyalkoxylated chain of the co-surfactant comprises from 10 to 200 ethylene oxide/propylene oxide units.

3. The immunogenic composition according to claim 1, further comprising an immunostimulating agent.

4. The immunogenic composition according to claim 1, further comprising:
   a biological targeting ligand either grafted or not on the co-surfactant, and/or
   an agent of interest selected from an optical agent or a physical agent, and/or
   a cationic surfactant.

5. The immunogenic composition according to claim 1, for which the viscosity is more than 0.1 Pa·s.

6. A drug comprising immunogenic composition of claim 1.

7. The immunogenic composition according to claim 1, wherein $A_2$ represents NH.

* * * * *

SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Amino acids 257 to 264 of ovalbumin

<400> SEQUENCE: 1

Ser Ile Ile Asn Phe Glu Lys Leu
1               5

<210> SEQ ID NO 2
<211> LENGTH: 17
<212> TYPE: PRT
<213> ORGANISM: Artificial Sequence
<220> FEATURE:
<223> OTHER INFORMATION: Amino acids 323 to 339 of ovalbumin

<400> SEQUENCE: 2

Ile Ser Gln Ala Val His Ala Ala His Ala Glu Ile Asn Glu Ala Gly
1               5                   10                  15

Arg

<210> SEQ ID NO 3
<211> LENGTH: 9
<212> TYPE: PRT
<213> ORGANISM: Artificial Sequence
<220> FEATURE:
<223> OTHER INFORMATION: Peptide of the modified ovalbumin
<220> FEATURE:
<221> NAME/KEY: MISC_FEATURE
<222> LOCATION: (1)..(1)
<223> OTHER INFORMATION: Xaa is a maleimide-serine
<220> FEATURE:
<221> NAME/KEY: MISC_FEATURE
<222> LOCATION: (9)..(9)
<223> OTHER INFORMATION: Xaa is a lysine-6-carboxy-fluorescein

<400> SEQUENCE: 3

Xaa Ile Ile Asn Phe Glu Lys Leu Xaa
1               5

<210> SEQ ID NO 4
<211> LENGTH: 17
<212> TYPE: PRT
<213> ORGANISM: Artificial Sequence
<220> FEATURE:
<223> OTHER INFORMATION: Peptide of the modified ovalbumin
<220> FEATURE:
<221> NAME/KEY: MISC_FEATURE
<222> LOCATION: (1)..(1)
<223> OTHER INFORMATION: Xaa is a maleimide-isoleucine
<220> FEATURE:
<221> NAME/KEY: MISC_FEATURE
<222> LOCATION: (17)..(17)
<223> OTHER INFORMATION: Xaa is an arginine-carboxytetramethylrhodamine

<400> SEQUENCE: 4

Xaa Ser Gln Ala Val His Ala Ala His Ala Glu Ile Asn Glu Ala Gly
1               5                   10                  15

Xaa